US010357452B2

(12) United States Patent
Goren et al.

(10) Patent No.: US 10,357,452 B2
(45) Date of Patent: *Jul. 23, 2019

(54) TREATMENT OF SEXUAL DYSFUNCTION

(71) Applicant: ReJoy, Irvine, CA (US)

(72) Inventors: Ofer A. Goren, Irvine, CA (US); John McCoy, Irvine, CA (US)

(73) Assignee: Rejoy, Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/012,065

(22) Filed: Jun. 19, 2018

(65) Prior Publication Data
US 2018/0296471 A1 Oct. 18, 2018

Related U.S. Application Data

(63) Continuation of application No. 15/303,578, filed as application No. PCT/US2016/036970 on Jun. 10, 2016, now Pat. No. 10,064,816.

(60) Provisional application No. 62/317,698, filed on Apr. 4, 2016, provisional application No. 62/297,598, filed on Feb. 19, 2016, provisional application No. 62/222,494, filed on Sep. 23, 2015, provisional application No. 62/213,927, filed on Sep. 3, 2015, provisional application No. 62/211,470, filed on Aug. 28, 2015, provisional application No. 62/203,728, filed on Aug. 11, 2015, provisional application No. 62/188,233, filed on Jul. 2, 2015, provisional application No. 62/175,806, filed on Jun. 15, 2015, provisional application No. 62/174,262, filed on Jun. 11, 2015.

(51) Int. Cl.
A61K 8/06 (2006.01)
A61K 9/00 (2006.01)
A61K 31/137 (2006.01)
A61K 31/4174 (2006.01)
A61K 31/166 (2006.01)
A61K 31/221 (2006.01)
A61K 31/4178 (2006.01)
A61K 31/439 (2006.01)
A61K 31/445 (2006.01)
A61K 31/465 (2006.01)
A61P 15/00 (2006.01)

(52) U.S. Cl.
CPC .......... A61K 9/0041 (2013.01); A61K 9/0009 (2013.01); A61K 9/0014 (2013.01); A61K 31/137 (2013.01); A61K 31/166 (2013.01); A61K 31/221 (2013.01); A61K 31/4174 (2013.01); A61K 31/4178 (2013.01); A61K 31/439 (2013.01); A61K 31/445 (2013.01); A61K 31/465 (2013.01); A61P 15/00 (2018.01)

(58) Field of Classification Search
CPC .. A61K 9/0041; A61K 9/0009; A61K 31/137; A61K 31/4174
See application file for complete search history.

(56) References Cited

U.S. PATENT DOCUMENTS

| 4,034,109 | A | 7/1977 | Rowsell et al. | |
| 4,853,216 | A * | 8/1989 | Koslo | A61K 8/41 424/73 |
| 5,055,456 | A | 10/1991 | Harris et al. | |
| 5,750,141 | A | 5/1998 | Roberts et al. | |
| 5,922,341 | A | 7/1999 | Smith et al. | |
| 6,294,517 | B1 | 9/2001 | Garvey et al. | |
| 6,747,008 | B1 | 6/2004 | Rodgers et al. | |
| 8,114,898 | B2 | 2/2012 | Shanler et al. | |
| 10,064,816 | B2 * | 9/2018 | Goren | A61K 31/137 |
| 2004/0198706 | A1 | 10/2004 | Carrara et al. | |
| 2005/0216880 | A1 | 9/2005 | Erickson et al. | |
| 2006/0110415 | A1 * | 5/2006 | Gupta | A61K 8/0212 424/401 |
| 2006/0252734 | A1 * | 11/2006 | Woodward | A61K 31/519 514/170 |
| 2007/0287733 | A1 | 12/2007 | Snorrason | |
| 2008/0011314 | A1 | 1/2008 | Arroyo et al. | |
| 2009/0068287 | A1 | 3/2009 | Welsh et al. | |
| 2009/0306026 | A1 | 12/2009 | Tuiten et al. | |
| 2012/0316246 | A1 | 12/2012 | Fahl et al. | |
| 2013/0199348 | A1 | 8/2013 | Aberizk | |
| 2014/0011774 | A1 | 1/2014 | Dalton et al. | |
| 2017/0135988 | A1 | 5/2017 | Goren et al. | |
| 2017/0165253 | A1 | 6/2017 | Goren et al. | |
| 2017/0333316 | A1 | 11/2017 | Goren et al. | |
| 2018/0078499 | A1 | 3/2018 | Goren et al. | |

FOREIGN PATENT DOCUMENTS

| WO | 97/04764 | 2/1997 |
| WO | 2004/041259 | 5/2004 |
| WO | 2010/123184 | 10/2010 |
| WO | 2016/077744 | 5/2016 |

OTHER PUBLICATIONS

International Search Report and Written Opinion for PCT/US2016/36970 dated Sep. 9, 2016.
Allahdadi et al., "Female Sexual Dysfunction: Therapeutic Options and Experimental Challenges," Cardiovasc Hematol Agents Med Chem., (Oct. 2009), vol. 7, No. 4, pp. 260-269.
Coon et al., "The Nature of the Pilomotor Response to Acetylcholine; Some Observations on the Pharmacodynamics of the Skin," The journal of Pharmacology and Experimental Therapeutics, (1939), vol. 68, Issue 3, pp. 301-311.
Dave et al., "Transpapillary Drug Delivery to the Breast," PLoS ONE, (Dec. 29, 2014), vol. 9, No. 12, pp. 1-16.

(Continued)

Primary Examiner — Micah Paul Young
(74) Attorney, Agent, or Firm — Buchanan Ingersoll & Rooney PC

(57) ABSTRACT

Compositions and methods for treating sexual dysfunction and enhancing sexual satisfaction using topical application of a therapeutic agent such as an alpha-1 adrenergic receptor agonist to the nipple-areola complex are disclosed.

50 Claims, No Drawings

(56) References Cited

OTHER PUBLICATIONS

Eglen et al., "Muscarinic Acetylcholine receptor Subtypes in Smooth Muscle," Trends in Pharmacological Sciences, (Apr. 1994), vol. 15, Issue 4, pp. 114-119.
Galitovskiy et al., "Muscle Sarcomas and Alopecia in A/J Mice Chronically Treated with Nicotine," Life Sciences, (Nov. 27, 2012), vol. 91, No. 21-22, pp. 1109-1112.
Harrison et al., "Self-Reports of Nipple Erection in Emotional and Somatic Contexts," The Psychological Record, (Jul. 2013), vol. 63, pp. 1-12.
Heatherton et al., "Development and Validation of a Scale for Measuring State Self-Esteem," Journal or Personality and Social Psychology, (1991), vol. 60, No. 6, pp. 895-910.
Hellmann, "The Isolated Pilomotor Muscles as an in Vitro Preparation," The Journal of Physiology, (Dec. 1963), vol. 169, No. 3, pp. 603-620.
Karlsson et al., "Snake Toxins with High Selectivity for Subtypes of Muscarinic Acetylcholine Receptors," Biochimie, (Sep.-Oct. 2000), vol. 82, No. 9-10, pp. 793-806.
Levin, "The Breast/Nipple/Areola Complex and Human Sexuality," Sexual and Relationship Therapy, (2006), vol. 21, Issue 2, pp. 237-249. (Abstract Only).
Levin et al., "Nipple/Breast Stimulation and Sexual Arousal in Young Men and Women," The Journal of Sexual Medicine, (May 2006), vol. 3, Issue 3, pp. 450-454. (Abstract Only).
Lewis et al., "Observations Upon a Pilomotor Reaction in Response to Faradism," The Journal of Physiology, (Oct. 5, 1927), vol. 64, Issue 1, pp. 87-106.
Moftah et al., "Glutathione Peroxidase and Malondialdehyde in skin Lesions of Acne Vulgaris," The Journal of the Egyptian Women's Dermatologic Society, (Jan. 2011), vol. 8, Issue 1, pp. 25-29.
Moser, "Comparisons of the Acute Effects of Cholinesterase Inhibitors Using a Neurobehavioral Screening Battery in Rats," Neurotoxicology and Teratology, (Nov.-Dec. 1995), vol. 17, Issue 6, pp. 617-625.
Piascik et al., "α1-Adrenergic Receptors: New Insights and Directions," The Journal of Pharmacology and Experimental Therapeutics, (2001), vol. 298, No. 2, pp. 403-410.
Rosenberg, "Rosenberg's Self-Esteem Scale," Society and the adolescent self-image, Princeton University Press, Princeton NJ (1965), accessed at www.wwnorton.com/college/psych/psychsci/media/rosenberg.htm on Mar. 13, 2017.
Rothman et al., "Axon Reflex Responses to Acetyl Choline in the Skin," The Journal of Investigative Dermatology, (1940) vol. 3, pp. 79-97.
Santos et al., "Drug Discovery for Alopecia: Gone Today, Hair Tomorrow," Expert Opinion on Drug Discovery, (2015), vol. 10, No. 3, pp. 269-292.
Schlenz et al., "Mastopexy and Breast Reduction," Shiftman, M.A., Ed., Springer-Verlag, Berlin, 2009, Chapter 79, pp. 618-619.
Siepmann et al., "The Quantitative Pilomotor Axon-Reflex Test (QPART)—A Technique to Assess Autonomic Nerve Fiber Function (Po5.197)," Neurology (Apr. 25, 2012), vol. 78, No. 1 Supplement Po5.197. (Abstract Only).
Siepmann et al., "Quantitative Pilomotor Axon Reflex Test: A Novel Test of Pilomotor Function," Archives of Neurology, (2012), vol. 69, No. 11, pp. 1488-1492.
Smelser et al., "Field use of Hair Epilation Force in Nutrition Status Assessment," The American Journal of Clinical Nutrition, (Feb. 1982), vol. 35, No. 2, pp. 342-346.
Stein et al., "Nipple Stimulation for Labor Augmentation," The Journal of Reproductive Medicine, (Jul. 1990), vol. 35, No. 7, pp. 710-714. (Abstract Only).
Wright et al., "Female Sexual Dysfunction," Medical Clinics of North America, (May 2015), vol. 99, Issue 3, pp. 607-628. (Abstract Only).
Wyness et al., "Trichotillometry: The Reliability and Practicality of Hair Pluckability as a Method of Nutritional Assessment," Nutrition Journal, (May 2007), vol. 6, No. 9, pp. 1-6.
Extended European Search Report dated Dec. 10, 2018 for Application No. 16808412.7.
Non Final Office Action dated Jan. 25, 2019 for U.S. Appl. No. 15/354,703.
Levin, R. J., The breast/nipple/areola complex and human sexuality, 2006, Sexual and Relationship Therapy, 237-249, vol. 21, No. 2, British Association for Sexual and Relationship Therapy.
Final Office Action issued in U.S. Appl. No. 15/354,703 dated Jul. 6, 2018.

* cited by examiner

TREATMENT OF SEXUAL DYSFUNCTION

CROSS-REFERENCES TO RELATED APPLICATIONS

This application is related to and claims the benefit of co-pending U.S. patent application Ser. No. 15/303,578 filed on Oct. 12, 2016, which claims the benefit of priority to International Patent Application No. PCT/US16/36970 filed on Jun. 10, 2016, which claims the benefit of U.S. Provisional Application No. 62/317,698 filed on Apr. 4, 2016, 62/297,598 filed on Feb. 19, 2016, U.S. Provisional Application No. 62/222,494 filed on Sep. 23, 2015, U.S. Provisional Application No. 62/213,927 filed on Sep. 3, 2015, U.S. Provisional Application No. 62/211,470 filed on Aug. 28, 2015, U.S. Provisional Application No. 62/203,728 filed on Aug. 11, 2015, U.S. Provisional Application No. 62/188,233 filed on Jul. 2, 2015, U.S. Provisional Application No. 62/175,806 filed on Jun. 15, 2015, and U.S. Provisional Application No. 62/174,262 filed on Jun. 11, 2015, the entire content of each is incorporated herein by reference.

TECHNICAL FIELD

The present disclosure relates to methods to treat sexual dysfunction, particularly female sexual dysfunction, and related disorders pertaining to sexual activity and sexual satisfaction, and methods to enhance sexual satisfaction, particularly female sexual satisfaction.

BACKGROUND DISCUSSION

Female sexual dysfunction (FSD) is a prevalent problem, afflicting approximately 40% of women. There are few treatment options. See Kyan J. Allandadi et al., "Female Sexual Dysfunction: Therapeutic Options and Experimental Challenges," Cardiovasc Hematol Agents Med Chem. 2009 October; 7(4): 260-269. FSD can be classified under many subtypes. For example, female sexual arousal disorder (FSAD) is a disorder characterized by a persistent inability to attain sexual arousal or to maintain arousal until the completion of a sexual activity. Female Sexual Interest/Arousal Disorder (FSIAD) is a diagnosis found when a subject experiences a lack of or significantly reduced sexual interest or arousal. Female hypoactive sexual desire disorder (FHSDD) is a general loss of interest in sexual activity. Other subtypes exist, for example, anorgasmia, a difficulty achieving orgasm. Currently, off-label use of testosterone has been prescribed. A therapy approved by the FDA in August 2015 is the Sprout Pharmaceuticals, Inc. product Addyi™ (flibanserin 100 mg), a once-daily, non-hormonal pill for the treatment of acquired, generalized hypoactive sexual desire disorder in premenopausal women. In addition, there are several drugs that were the subject of clinical trials that affect signaling in the brain. See Wright, J. J., O'Connor, K. M. (2015), "Female sexual dysfunction," Medical Clinics of North America, 99(3), 607-628. Because both hormonal and psycho-affective drugs can be associated with serious negative side effects, alternative treatment options would be desired for treating this prevalent condition.

The arousal phase of the female sexual response cycle involves genital mechanisms, such as clitoral, labial, and vaginal engorgement, as well as non-genital peripheral mechanisms, such as increases in body secretions, cutaneous vasodilation, and nipple erection. Nipple erection occurs via activation of adrenergic nerves. Smooth muscles in the nipple areola complex are contracted, thereby erecting the nipple. The role of nipple stimulation in influencing sexual desire and arousal in women prior to and during intercourse has been reported in the literature. Eighty-two percent of surveyed women report that stimulation of their nipples caused or enhanced their sexual arousal. See Levin, R., Meston, C. (2006), "Nipple/Breast stimulation and sexual arousal in young men and women," Journal of Sexual Medicine, 3(3), 450-454; Levin, R. (2006), "The breast/nipple/areola complex and human sexuality," Sexual and Relationship Therapy, 21(2), 237-249. In addition, stimulation of a women's nipple has been shown to correlate with increased oxytocin levels in blood serum. See Stein, J. L., Bardeguez, A. D., Verma, U. L., Tegani, N. (1990), "Nipple stimulation for labor augmentation," Journal of Reproductive Medicine, 35(7), 710-714. Oxytocin is a peptide hormone shown to play a role in sexual satisfaction and desire.

U.S. Pat. No. 4,853,216 (Koslo et al.) reports topical application of alpha-1 adrenergic receptor agonists ("A1AR agonists") to a hair-bearing skin area to facilitate the physical or chemical handling of the hair. The purpose is to activate the pilomotor effect and erect the hair on the skin. This may be applied as a pretreatment prior to shaving or incorporated into a shaving composition, such as shaving cream. U.S. Pat. No. 4,853,216 discloses that suitable A1AR agonists include phenylephrine and methoxamine. See U.S. Pat. No. 4,853,216 at col. 2 lines 46-48. WO2004041259 (Thurlow et al.) describes the use of alpha 1 adrenergic receptor antagonists for the treatment of FSD. The reference does not describe application of the antagonist to at least a portion of the nipple-areola complex, and focuses rather on inhibitors of receptors in the vaginal tissue. It is unexpected from this teaching that an A1AR agonist would be useful for treatment of FSD when applied to at least a portion of the nipple-areola complex.

A1AR agonists bind to α1-receptors on vascular smooth muscle and induce smooth muscle cell contraction, thus mimicking the effects of sympathetic neurons activation of smooth muscles via adrenergic receptors. Phenylephrine is a selective A1AR agonist. Phenylephrine is used as a decongestant, for which it is sold as an oral medicine or a nasal spray. Phenylephrine is also sold as a topical ointment to prevent or reduce symptoms of hemorrhoids. Phenylephrine is used as an eye drop to dilate the pupil to facilitate visualization of the retina. US Patent Application Pub. 2004/0198706 (Carrara et al.) discloses formulations for providing transdermal or transmucosal delivery of active agents. The formulations treat symptoms of hormonal disorders including female sexual desire disorder. The active agents may be selected from a large group of therapeutic agents, one of which is phenylephrine. The reference does not describe application of the transdermal or transmucal dosage forms to the nipple-areola complex. It is unexpected from this teaching that an A1AR agonist such a phenylephrine would be useful for treatment of FSD when applied to the nipple-areola complex.

SUMMARY

The present disclosure concerns a method of treating sexual dysfunction, in some embodiments treating female sexual dysfunction, the method comprising applying a therapeutically effective amount of a composition comprising an alpha-1 adrenergic receptor agonist topically to a nipple-areola complex of a subject in need of such treatment. In another embodiment, the disclosure concerns a method of reducing or alleviating a symptom of sexual dysfunction, in some embodiments a symptom of female sexual dysfunction, the method comprising applying a therapeutically effective amount of a composition comprising an alpha-1 adrenergic receptor agonist topically to a nipple-areola complex of a subject in need of such treatment. In yet another embodiment, the disclosure concerns a method for enhancing sexual satisfaction in a subject, in some embodiments a female subject, comprising applying an effective amount of a composition comprising an alpha-1 adrenergic receptor agonist topically to a nipple-areola complex of the subject. In a further embodiment, the disclosure concerns a method of causing erection of nipples, increasing nipple sensitivity, increasing duration of orgasm, reducing time to orgasm, and/or increasing oxytocin release related to sexual activity in a subject, in some embodiments a female subject, comprising applying an effective amount of a composition comprising an alpha-1 adrenergic receptor agonist topically to a nipple-areola complex of the subject. The disclosure also concerns compounds and compositions for use in any of the methods disclosed herein.

DETAILED DESCRIPTION

Methods of Use

The present disclosure relates to methods to treat or reduce sexual dysfunction and related disorders pertaining to sexual activity and sexual satisfaction, and methods to enhance sexual satisfaction, in some embodiments female sexual satisfaction. As used herein, the terms "female sexual dysfunction" or "FSD" refer generally to the impairment of the sexual function in a female. Sexual dysfunction in females includes inhibited orgasm. Female sexual dysfunction includes, but is not limited to, a number of categories of diseases, conditions and disorders including female hypoactive sexual desire disorder (FHSDD or HSDD, used interchangeably herein), female orgasmic disorder (FOD), sexual anhedonia, female sexual interest/arousal disorder (FSIAD), and female sexual arousal disorder (FSAD). Hypoactive sexual desire disorder includes a disorder in which sexual fantasies and desire for sexual activity are persistently or recurrently diminished or absent, causing marked distress or interpersonal difficulties. Sexual anhedonia includes decreased or absent pleasure in sexual activity. Sexual arousal disorder can be caused by reduced estrogen, illness, or treatment with diuretics, antihistamines, antidepressants, or antihypertensive agents. The woman can experience mild, moderate, or severe FSD.

In one embodiment, FSD, FSAD, FOD and FHSDD are as defined in the Diagnostic and Statistical Manual of Mental Disorders (DSM), 4th edition, the contents of which definitions are incorporated herein by reference. In another embodiment, the disorder is female sexual interest/arousal disorder (FSIAD), which encompasses FSAD and FHSDD. FOD and FSIAD are defined in the Diagnostic and Statistical Manual of Mental Disorders (DSM), 5th edition, the contents of which definitions are hereby incorporated herein by reference. The diagnostic criteria for FSIAD include a lack of, or significantly reduced, sexual interest/arousal, as manifested by at least three of the following: (1) absent/reduced interest in sexual activity; (2) absent/reduced sexual/erotic thoughts or fantasies; (3) no/reduced initiation of sexual activity, and typically unreceptive to a partner's attempts to initiate; (4) absent/reduced sexual excitement/pleasure during sexual activity in almost all or all sexual encounters; (5) absent/reduced sexual interest/arousal in response to any internal or external sexual/erotic cues; and (6) absent/reduced genital or nongenital sensations during sexual activity in almost all or all sexual encounters. In FSIAD, these symptoms have persisted for a minimum duration of approximately six months and cause the subject significant distress. The diagnostic criteria for FOD are as follows:

A. Presence of either of the following symptoms and experienced on almost all or all (approximately 75%-100%) occasions of sexual activity (in identified situational contexts or, if generalized, in all contexts): (1). Marked delay in, marked infrequency of, or absence of orgasm. (2). Markedly reduced intensity of orgasmic sensations.

B. The symptoms in Criterion A have persisted for a minimum duration of approximately 6 months.

C. The symptoms in Criterion A cause clinically significant distress in the individual.

D. The sexual dysfunction is not better explained by a nonsexual mental disorder or as a consequence of severe relationship distress (e.g., partner violence) or other significant stressors and is not attributable to the effects of a substance/medication or another medical condition.

The diagnosis of FOD also asks the clinician to specify whether (1) Lifelong: The disturbance has been present since the individual became sexually active or (2) Acquired: The disturbance began after a period of relatively normal sexual function. Also, the clinician is to specify whether (1) Generalized: Not limited to certain types of stimulation, situations, or partners or (2) Situational: Only occurs with certain types of stimulation, situations, or partners. The clinician is to specify if the subject never experienced an orgasm under any situation. The clinician is also to specify the current severity: (1) Mild: Evidence of mild distress over the symptoms in Criterion A, (2) Moderate: Evidence of moderate distress over the symptoms in Criterion A, (3) Severe: Evidence of severe or extreme distress over the symptoms in Criterion A. As reported in the Diagnostic and Statistical Manual of Mental Disorders (DSM), 5th edition, page 431, selective serotonin reuptake inhibitors (SSRIs) are known to delay or inhibit orgasm in women.

According to certain of the methods disclosed herein, to treat female sexual dysfunction disorder(s) or to enhance female sexual satisfaction, a topical composition of a therapeutic agent is applied to the woman's nipple-areola complex. In one aspect of the invention there is a method of treating FSD, preferably FSIAD, FSAD, FSOD, or FHSDD, comprising administering to a subject in need of such treatment an effective amount of a therapeutic agent as defined herein topically to the nipple-areola complex. As used herein, applying a composition to a nipple-areola complex includes applying to the nipple, the areola, or both the nipple and the areola, and to all or a portion of the nipple, the areola, or both the nipple and the areola. For example, the composition may be applied to the areola area only, the base of the nipple only, to half the areola only or applied to more than half of the areola and not the nipple. In one embodiment, the composition is applied to only one of a subject's nipple-areola complexes. The term "nipple-areola complex" includes both the nipple and areola. The nipple-areola complex varies in dimension among individuals. The female nipple-areola complex is located at the prominence of the breast mound. See Anongporn Nimboriboonporn, "Nipple-areola complex reconstruction," *Gland Surgery* 2014; 3(1), pp. 35-42. The nipple itself may project as much as greater than or equal to 1 cm, with a diameter of approximately 4-7 mm. The areola consists of pigmented skin surrounding the nipple proper and is on average approximately 4.2-4.5 cm in diameter. The smooth muscle morphology in the nipple-areola complex is described, for example, in M. Tezer, et al., "Smooth muscle morphology in the nipple-areola complex," J. Morphol. Sci., 2011, vol. 28, no. 3, p. 171-175.

In other embodiments, the invention is directed to methods of enhancing female sexual satisfaction, causing erection of nipples, increasing nipple sensitivity, increasing duration of orgasm, reducing time to orgasm, increasing intensity of orgasm and/or increasing oxytocin release related to sexual activity by administering a therapeutic agent according to the present disclosure topically to the nipple areola complex of a female subject. In one embodiment, the invention is directed to methods for the manufacture of compositions, particularly pharmaceutical compositions, for the treatment or reduction of any of the disorders or conditions recited herein comprising mixing the therapeutic agent with a pharmaceutically acceptable excipient, such as water, mineral oil, or a surfactant. In one embodiment, the method comprises (1) applying an alpha 1 adrenergic receptor agonist (e.g., without limitation, synephrine) on a test site on the skin of a person; wherein the test site is not in the nipple areola complex; and (2) 30 to 60 minutes after applying, observing whether the person's skin shows goosebumps or pilioerection at the site; wherein if pilioerection or goosebumps are observed, then diagnosing the person as likely to be a successful candidate for use of the alpha 1 adrenergic receptor agonist for any of the many methods of treatment or prevention described herein. This method may be combined with any of the other methods of treatment or prevention described herein to provide an initial diagnosis of those people most likely to benefit from the treatment and prevention described. In such combination methods, the treatment steps only proceed if the person's skin shows goosebumps or pilioerection at the test site. The step of application to a site on the skin may be, in one embodiment, applying a bandage or patch coated with the alpha 1 adrenergic receptor agonist to the person's arm or thigh. In another embodiment of any composition or method involving an alpha 1 adrenergic receptor agonist, the agonist is synephrine or phenylephrine.

The subjects to be treated with the present invention may be pre-, per- and post-menopausal women or men. In one embodiment, the woman is concomitantly on hormone replacement therapy. In another embodiment she is not on concomitant hormone replacement therapy. The methods disclosed may be useful for women who have diminished breast sensation, such as women having low nipple sensitivity, which may occur after breast surgery or breast implants. In another embodiment, the disclosed methods may be used in women with high breast or nipple-areola sensitivity; such as to enhance sexual satisfaction.

In another embodiment, the subjects to be treated is a mammal, such as non-human primates (particularly higher primates), sheep, dog, rodent (e.g. mouse or rat), guinea pig, goat, pig, cat, rabbits, cow, and panda. Treatment in non-human mammals may be desirable to accelerate conception during mating. Treatment may also be desirable to induce labor in a mammal, including a human.

In one embodiment, the subject to be treated is a human or animal concomitantly taking one or more SSRI or antidepressants, such as antidepressants used in the treatment of major depressive disorder and anxiety disorders. SSRIs may cause a variety of sexual dysfunction, such as anorgasmia, erectile dysfunction, diminished libido, genital numbness, and sexual anhedonia (pleasureless orgasm). To minimize or reduce these side effects, one of the therapeutic agents of the present disclosure according to any of the methods of administration disclosed herein may also be administered to the subject concomitantly with the SSRI therapy. By "concomitantly" is meant herein to be administered in the same day, week or month, not necessarily at the same time of day, however. SSRIs include the following: citalopram, fluvoxamine, escitalopram, paroxetine, sertraline, fluoxetine, and dapoxetine. The compositions and methods of the present disclosure may also be used with a subject who concomitantly is taking tricyclic antidepressants or serotonin-noradrenaline reuptake inhibitors (SNRIs). Examples of SNRIs include the following: venlafaxine; desvenlafaxine, duloxetine, milnacipran, levomilnacipran, and sibutramine.

The formulations of therapeutic agent described herein may be applied once every one, two, three, four, six, eight, ten or twelve hours, or once daily, twice daily, or once every other day. The frequency of administration may be determined by one skilled in the art using pharmacokinetic data available or generated using standard procedures. Routine pharmacological testing may be performed to determine if dosages of more than once or twice daily are advisable and if so the amount of each dosage, in view of the potential for a rebound effect. It should be noted that increased sexual arousal can be delayed with respect to nipple erection after the application of the composition described herein. For example, increased sexual arousal can occur about 10-45 minutes after nipple erection. The formulations of therapeutic agent described herein may be applied as needed. In one embodiment, the formulation is applied prior to a sexual activity, such as about 0.25, 0.5, 1.0, 1.5, 2.0, 2.5, 3.0, 4.0, 5.0, or 6.0 hours prior to sexual activity, or between 0.25-1.0, 0.5-1.0, 0.5-1.5, 1.0-2.0, or 1.0-4.0 hours prior to sexual activity. Examples of sexual activities include, but are not limited to, foreplay, sexual intercourse, and masturbation. In case of sensitivity of the nipple-areola complex to the formulation, it may be advisable that following use the next administration occur after 48-72 hours has passed.

As used herein, the terms "treat," "treatment," or "treating" refer to therapeutic treatments, wherein the object is to reverse, alleviate, ameliorate, inhibit, slow down or stop the progression or severity of a disease or condition, e.g., FSD. The term "treating" includes reducing or alleviating at least one adverse effect or symptom of a disease or condition, e.g., FSD. Treatment is generally "effective" if one or more symptoms are reduced. That is, "treatment" includes the improvement of symptoms. Beneficial or desired clinical results include, but are not limited to, alleviation of one or more symptom(s) and diminishment of extent of disease. For example, treatment of FSD is considered effective if the number of satisfying sexual events (SSE) is increased from baseline in a sampled time (e.g. 4 weeks), in a significant manner. Other established metrics to determine treatment efficacy for FSD include, for example, FSFI (female sexual function index), SAL (Sexual Activity Log), SAR (Sexual Activity Record), FSDS (Female Sexual Distress Scale), and the FSDS-R (Female Sexual Distress Scale Revised). Treatment may occur even if nipple erection is not obtained. Setting the smooth muscle underlying the nipple-areola complex without nipple erection is believed sufficient to elicit the desirable biological response in a subject, such as a female subject, and therefore to "treat" or "enhance" according to the methods disclosed herein.

In one embodiment, a therapeutic effect is seen when the difference from baseline is a "minimally important difference" or "MIN" defined in: DeRogatis, L. R., Graziottin, A., Bitzer, J., Schmitt, S., Koochaki, P. E., Rodenberg, C. (2009), "Clinically relevant changes in sexual desire, satisfying sexual activity and personal distress as measured by the profile of female sexual function, sexual activity log, and personal distress scale in postmenopausal women with hypoactive sexual desire disorder," Journal of Sexual Medicine, 6, 175-183, the contents of which are incorporated herein by reference. Such a change may be small but meaningful to subjects.

Therapeutic Agents

In one embodiment, the therapeutic agent used in the inventive methods herein is an A1AR agonist. "Alpha 1 adrenergic receptor agonist" or "A1AR agonist" refers to a ligand that binds the alpha 1 adrenergic receptor on smooth muscle cells and activates smooth muscle contraction. In some embodiments, the AIAR agonist is selective for the alpha-1 adrenergic receptor. Additionally, the term "alpha 1 adrenergic receptor agonist" can include agents that when applied will induce the release of endogenous alpha 1 adrenergic receptor agonists (e.g. epinephrine) that activates smooth muscle contraction or agents that when applied inhibit the "re-uptake" or degradation of endogenous alpha 1 adrenergic receptor agonists (e.g. epinephrine) that activates smooth muscle contraction. In another embodiment, the therapeutic agent used is a "smooth muscle agonist," which is an agent that promotes or results in contraction of the smooth muscle including smooth muscle of the nipple-areola complex. Thus, an alpha 1 adrenergic receptor agonist that promotes or results in smooth muscle contraction is a smooth muscle agonist, but so also are, e.g., an alpha 2 adrenergic receptor agonist that promotes smooth muscle contraction, agents that that induce the release of endogenous alpha 2 adrenergic receptor agonist that results in smooth muscle contraction, and agents that inhibit the re-uptake or degradation of endogenous alpha 2 adrenergic receptor agonists that activate smooth muscle contraction. Suitable A1AR agonists for use in the present description include without limitation phenylephrine, phenylephrine pivalate, amediphrine, synephrine, cirazoline, desvenlafaxine, etilfrine, metaraminol, methoxamine, naphazoline, oxymetazoline, pseudoephrine, m-synephrine, p-synephrine, octopamine, hordenine, tetrahydrozoline, isomepheptene, metaraminol, nicergoline, ergonovine, levonordefrin, phendimetrazine, methoxamine, midodrine, clonidine, pergolide, xylometazoline, droxidopa, epinephrine, mephentermine, 4-methoxyamphetamine, benzphetamine, naphazoline, apraclondine, bromocriptine, oxymetazoline, phenylpropanolamine, pseudoephedrine, dipivefrin, noradrenaline, and chloroethylclonidine. In certain embodiments, the A1AR agonist is synephrine, or is phenylephrine, synephrine, oxymetazoline, or methoxamine. In one embodiment, the therapeutic agent is norepinephrine. Another suitable therapeutic agent for use in the inventive methods herein is extract of Bitter orange (*Citrus aurantium*), which contains synephrine alkaloids and para-octopamine. See Satoh, Y., Tashiro, S., Satoh, M., Fujimoto, Y., Xu, J. Y., and Ikekawa, T. [Studies on the bioactive constituents of Aurantii Fructus Immaturus]. Yakugaku Zasshi 1996; 116(3):244-250.

Additionally, derivatives of alpha 1 adrenergic receptor agonists can be utilized including derivatives of the compounds mentioned above. In other embodiments, a prodrug that is activated to become an A1AR agonist can be utilized. Midodrine, phenylephrine oxazolidine, and phenylephrine pivalate are examples of three such prodrugs. Phenylephrine pivalate is an A1AR agonist in addition to being a prodrug of phenylephrine. A particular prodrug can be activated by endogenous enzymes in the skin such as Caspase-1. Another embodiment is a method for reducing or ceasing erection of the nipple following administration of alpha-1 adrenergic receptor agonist(s) comprising applying a therapeutically effective amount of an alpha 1 adrenergic receptor antagonist or a beta adrenergic receptor agonist to the nipple areola complex. Such a method may be useful, for example, in the event of an overdose of alpha 1 adrenergic receptor agonist.

As used herein, a "prodrug" refers to compounds that can be converted via some chemical or physiological process (e.g., enzymatic processes and metabolic hydrolysis) to a therapeutic agent. Thus, the term "prodrug" also refers to a precursor of a biologically active compound that is pharmaceutically acceptable. A prodrug may be inactive when administered to a subject, i.e. an ester, but is converted in vivo to an active compound, for example, by hydrolysis to the free carboxylic acid or free hydroxyl. The prodrug compound often offers advantages of solubility, tissue compatibility or delayed release in an organism. The term "prodrug" is also meant to include any covalently bonded carriers, which release the active compound in vivo when such prodrug is administered to a subject. Prodrugs of an active compound may be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a subject, cleaves to form a free hydroxy, free amino or free mercapto group, respectively. Examples of prodrugs include, but are not limited to, acetate, formate and benzoate derivatives of an alcohol or acetamide, formamide and benzamide derivatives of an amine functional group in the active compound and the like. See Harper, "Drug Latentiation" in Jucker, ed. *Progress in Drug Research* 4:221-294 (1962); Morozowich et al, "Application of Physical Organic Principles to Prodrug Design" in E. B. Roche ed. *Design of Biopharmaceutical Properties through Prodrugs and Analogs*, APHA Acad. Pharm. Sci. 40 (1977); *Bioreversible Carriers in Drug in Drug Design, Theory and Application*, E. B. Roche, ed., APHA Acad. Pharm. Sci. (1987); *Design of Prodrugs*, H. Bundgaard, Elsevier (1985); Wang et al. "Prodrug approaches to the improved delivery of peptide drug" in *Curr. Pharm. Design.* 5(4):265-287 (1999); Pauletti et al. (1997) Improvement in peptide bioavailability: Peptidomimetics and Prodrug Strategies, *Adv. Drug. Delivery Rev.* 27:235-256; Mizen et al. (1998) "The Use of Esters as Prodrugs for Oral Delivery of (3-Lactam antibiotics," *Pharm. Biotech.* II, 345-365; Gaignault et al. (1996) "Designing Prodrugs and Bioprecursors I. Carrier Prodrugs," *Pract. Med. Chem.* 671-696; Asgharnejad, "Improving Oral Drug Transport", in *Transport Processes in Pharmaceutical Systems*, G. L. Amidon, P. I. Lee and E. M. Topp, Eds., Marcell Dekker, p. 185-218 (2000); Balant et al., "Prodrugs for the improvement of drug absorption via different routes of administration", *Eur. J. Drug Metab. Pharmacokinet.*, 15(2): 143-53 (1990); Balimane and Sinko, "Involvement of multiple transporters in the oral absorption of nucleoside analogues", *Adv. Drug Delivery Rev.*, 39(1-3): 183-209 (1999); Browne, "Fosphenytoin (Cerebyx)", *Clin. Neuropharmacol.* 20(1): 1-12 (1997); Bundgaard, "Bioreversible derivatization of drugs—principle and applicability to improve the therapeutic effects of drugs," *Arch. Pharm. Chemi* 86(1): 1-39 (1979); Bundgaard H. "Improved drug delivery by the prodrug approach," *Controlled Drug Delivery* 17: 179-96 (1987); Bundgaard H. "Prodrugs as a means to improve the delivery of peptide drugs," *Arfv. Drug Delivery Rev.* 8(1): 1-38 (1992); Fleisher et al. "Improved oral drug delivery: solubility limitations overcome by the use of prodrugs," *Arfv. Drug Delivery Rev.* 19(2): 115-130

(1996); Fleisher et al. "Design of prodrugs for improved gastrointestinal absorption by intestinal enzyme targeting," *Methods Enzymol.* 112 (Drug Enzyme Targeting, Pt. A): 360-81, (1985); Farquhar D, et al., "Biologically Reversible Phosphate-Protective Groups," *Pharm. Sci.,* 72(3): 324-325 (1983); Freeman S, et al., "Bioreversible Protection for the Phospho Group: Chemical Stability and Bioactivation of Di(4-acetoxy-benzyl) Methylphosphonate with Carboxyesterase," *Chem. Soc., Chem. Commun.,* 875-877 (1991); Friis and Bundgaard, "Prodrugs of phosphates and phosphonates: Novel lipophilic alphaacyloxyalkyl ester derivatives of phosphate- or phosphonate containing drugs masking the negative charges of these groups," *Eur. J. Pharm. Sci.* 4: 49-59 (1996); Gangwar et al., "Pro-drug, molecular structure and percutaneous delivery," *Des. Biopharm. Prop. Prodrugs Analogs,* [*Symp.*] Meeting Date 1976, 409-21. (1977); Nathwani and Wood, "Penicillins: a current review of their clinical pharmacology and therapeutic use," *Drugs* 45(6): 866-94 (1993); Sinhababu and Thakker, "Prodrugs of anticancer agents," *Adv. Drug Delivery Rev.* 19(2): 241-273 (1996); Stella et al., "Prodrugs. Do they have advantages in clinical practice?" *Drugs* 29(5): 455-73 (1985); Tan et al. "Development and optimization of anti-HIV nucleoside analogs and prodrugs: A review of their cellular pharmacology, structure-activity relationships and pharmacokinetics," Adv. Drug Delivery Rev. 39(1-3): 117-151 (1999); Taylor, "Improved passive oral drug delivery via prodrugs," *Adv. Drug Delivery Rev.,* 19(2): 131-148 (1996); Valentino and Borchardt, "Prodrug strategies to enhance the intestinal absorption of peptides," *Drug Discovery Today* 2(4): 148-155 (1997); Wiebe and Knaus, "Concepts for the design of anti-HIV nucleoside prodrugs for treating cephalic HIV infection," *Adv. Drug Delivery Rev.:* 39(I-3):63-80 (1999); Waller et al., "Prodrugs," *Br. J. Clin. Pharmac.* 28: 497-507 (1989), which are incorporated by reference herein in their entireties.

Other agents or approaches can be used to contract the smooth muscle to erect nipples for the treatment of FSD or the enhancement of sexual satisfaction. As noted above, any agent or treatment that stimulates smooth muscle contraction is of potential use in methods of treating FSD or enhancing sexual satisfaction as described herein.

In one embodiment, the smooth muscle can be contracted by stimulating or activating a cold receptor. This is believed to stimulate the pilomotor reflex to result in contraction of the smooth muscle and erection of the nipple. A cold receptor can be stimulated, for example, by activating the TRPM8 channel. Exemplary agents that can stimulate a cold receptor include, but are not limited to, menthol and icilin. Compositions and methods for stimulating a cold receptor are disclosed, for example, in U.S. Pat. No. 4,034,109 (Rowsell et al.).

Where the smooth muscle is served by or associated with both noradrenergic fibers and a cholinergic system, agents that stimulate release of transmitters from these systems can be used to stimulate smooth muscle contraction. Thus, not only alpha 1 adrenergic agonists, but also cholinergic agonists, including, but not limited to acetylcholine and other neurotransmitters that stimulate smooth muscle contraction are contemplated for use in the methods and compositions described herein. The alpha 1 adrenergic receptor is a postsynaptic G protein-coupled receptor on the surface of smooth muscle cells. Agonists of other G protein-coupled receptors involved in smooth muscle contraction (e.g., postsynaptic alpha 2 adrenergic receptors) can also be used to stimulate contraction of the smooth muscles and thus erection of the nipple when applied to the nipple-areola complex.

Examples of agonists of the postsynaptic alpha 2 adrenergic receptor include but are not limited to, 4-NEMD, 7-Memarsanidine, agmatine, apraclonidine, brimonidine, clonidine, detomidine, dexmedetomidine, fadolmidine, guanabenz, guanfacine, lofexidine, marsanidine, medetomidine, methamphetamine, mivazerol, rilmenidine, romifidine, talipexole, tizanidine, tolonidine, xylazine, brimonidine, amitraz, chloroethylclonidine and xylometazoline. In some embodiments, an antagonist of the presynaptic alpha 2 adrenergic receptor that inhibits negative feedback of noradrenaline release from the presynaptic neuron, can also be used to stimulate smooth muscle cell contraction. Such antagonists include aripiprazole, asenapine, atipamezole, cirazoline, clozapine, efaroxan, idazoxan, lurasidone, melperone, minserin, mirtazapine, napitane, olanzapine, paliperidone, phenoxybenzamine, phentolamine, piribedil, rauwolscine, risperidone, rotigotine, quetiapine, norquetiapine, setipiline, tolazoline, yohimbine, ziprasidone, and zotepine. In some embodiments, an alpha 1 agonist/alpha 2 partial agonist, such as oxymetazoline, is contemplated for use with the methods described herein. To the extent that it would be disadvantageous to administer these or other agents systemically, they can be administered in a formulation that permits uptake by the smooth muscle of at least a portion of the nipple-areola complex in the dermis but limits systemic uptake.

It should be noted that the agonists and antagonists described herein also encompass their pharmaceutically acceptable inorganic or organic salts. Representative salts include the hydrobromide, hydrochloride, sulfate, bisulfate, phosphate, nitrate, acetate, succinate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. For example, phenylephrine may be administered in its hydrochloride salt form.

Formulations and Dosages

The present disclosure also pertains to pharmaceutical compositions of the therapeutic agents discussed herein. The formulations or compositions of the present disclosure include a therapeutically effective amount of a therapeutic agent and a pharmaceutically acceptable excipient. Formulation guidance may be found in Remington: The Science and Practice of Pharmacy, Pharmaceutical Press (2012), Allen (ed.). The compositions may be of any sort useful for topical delivery to the nipple-areola complex, such as, without limitation, a gel, cream, emulsion, transdermal patch, spray, ointment, or aerosol. In one preferred formulation, the composition is a gel. In some embodiments, the therapeutic agent is present in a transdermal patch that is sized and designed to fit smoothly around the nipple. The transdermal patch may provide immediate release or sustained release of the therapeutic agent. In another embodiment, the therapeutic agent is applied to a substrate such as a bandage having an exterior and an interior surface, where the interior surface is coated with the therapeutic agent and a surrounding adhesive section. The adhesive section preferably is adjacent to, but not comingled with, the coating of therapeutic agent. The substrate is then applied to the nipple areola complex such that the interior surface of the substrate is placed on the skin and therapeutic agent is in contact with the nipple areola complex. In one embodiment, this substrate is shaped like a donut with a circular shape having a central circle cut-out. The coated substrate is applied to the nipple-areola complex such that much of the nipple (at least 50%) is not in contact with the therapeutic agent because the nipple extends through the hole in the bandage. This embodiment is particularly desirable for patients for whom the nipple is particularly sensitive. In this embodiment, the substrate is ring shaped and comprises two surfaces, an exterior and an interior surface, the exterior surface preferably comprising a water-resistant plastic coating and the interior surface coated with the therapeutic agent along a central portion closest to the center of the ring and a circumferential surface extending along the broadest circumference of the substrate that contains an adhesive that provides adhesion, removably, to human skin surface. The therapeutic agent present on the substrate may be in a formulation that is a gel, solution, cream, etc. In one of these embodiments, the substrate coated with therapeutic agent is applied to the areola for 10, 15, 20, 25, 30, 40, or 45 minutes and then removed, or for less than 10, less than 15, less than 20, less than 25, less than 30, or less than 45 minutes and then removed. The substrate may be disposed after application. In other embodiments, the therapeutic agent can be included in ointments or other topical creams that could be applied to at least a portion of the nipple-areola complex so that it can be absorbed into the skin and stimulate the smooth muscle. In other embodiments, the therapeutic agent can be in a liquid spray or aerosol medium, such as a metered spray, such as is found for example in Evamist® estradiol transdermal spray. The spray may contain an alcohol, water, or a water/alcohol mixture as a vehicle for the therapeutic agent.

In some embodiments, the composition is provided in a delivery device that has a roller ball connected to a container holding the composition such that the composition may be applied to the nipple-areola complex by rolling the ball directly on the complex. For example, the roller ball device may have a generally cylindrical container that holds a liquid formulation of the therapeutic agent therein and has an open upper end and a lower end. A roller ball is rotatably disposed in the container and protrudes from the upper end of the container. A cap portion has a closed upper end and an open lower end. The lower end of the cap portion is removably coupled to the upper end of the container. Devices such as these are well known in the art. See, e.g., U.S. Pat. No. 6,095,708 (Butaud); U.S. Pat. No. 5,007,775 (Thompson); U.S. Pat. No. 4,664,547 (Rosenwinkel); U.S. Design Pat. 333,977 (Gatrost); and U.S. Design Pat. 292,069 (Keeler).

In one embodiment, the compositions are formulated for quick delivery through the dermis to the smooth muscles, such as for delivery of 60%, 70%, 75%, 80%, 85% or more of the therapeutic agent through the dermis within 5, 4, 3, 2 or 1 hour of application to the nipple-areola complex. In another embodiment, at least 80% of the therapeutic agent is delivered through the dermis on average after three hours as measured with an in vitro release test using a Franz cell such as discussed in the examples herein.

Formulations may be prepared according to the knowledge and skill of those in the art. In some embodiments, the compositions can further comprise a flavoring agent. One example of the flavoring agent is a sweetening agent, such as monoammonium glycyrrhizinate. In liquid and gel formulations, the bulk excipient that serves as a medium for conveying the active ingredient is the vehicle. Suitable vehicles for topical gels and creams include petrolatum and mineral oil.

Penetration enhancers may be used in the present compositions to increase the permeability of the dermal surface to a therapeutic agent, and are often proton accepting solvents such as dimethyl sulfoxide (DMSO) and dimethylacetamide. Chemical permeation enhancers facilitate drug permeation across the skin by increasing drug partitioning into the barrier domain of the stratum corneum and/or increasing drug diffusivity in the barrier domain of the stratum corneum. Several mechanisms of action are known: increasing fluidity of stratum corneum lipid bilayers, extraction of intercellular lipids, increase of drug's thermodynamic activity, increase in stratum corneum hydration, alteration of proteinaceous corneocyte components and others. Permeation enhancers are conventionally divided into several groups based on their chemical structure rather than the mechanism of action. More than 300 substances have been shown to have skin permeabilization potential. Enhancers fall into the following general categories: alcohols (ethanol, pentanol, benzyl alcohol, lauryl alcohol, propylene glycols and glycerol), fatty acids (oleic acid, linoleic acid, valeric acid and lauric acid), amines (diethanolamine and triethanolamine), esters (isopropyl palmitate, isopropyl myristate and ethyl acetate), amides (1-dodecylazacycloheptane-2-one [Azone®], urea, dimethylacetamide, dimethylformamide and pyrrolidone derivatives), hydrocarbons (alkanes and squalene), surfactants (sodium laureate, cetyltrimethylammonium bromide, Brij® nonionic polyoxyethylene surfactant, Tween® polyol and sodium cholate), terpenes (D-limonene, carvone and anise oil), sulfoxides (dimethyl sulfoxide) and phospholipids (lecithine). Hydration of the stratum corneum is important. A fully hydrated stratum corneum (under occlusion) presents lesser diffusional resistance to a drug than its dehydrated counterpart.

In some embodiments, the composition further comprises an exfoliating agent to promote abrasion of the surface of the skin to increase the permeability of the dermal surface to a therapeutic agent. Examples of the exfoliating agent include (1) inorganic and/or metallic particles such as: boron nitride, in body-centered cubic form (Borazon®); aluminosilicate (e.g. nepheline); zircon; mixed oxides of aluminum such as emery; zinc oxide; aluminum oxides such as aluminas or corundum; titanium oxide; titanium oxide coated mica; carbides, in particular silicon carbide (carborundum); or other metal oxides; metals, and metal alloys such as iron shot, steel shot, and in particular perlite; silicates such as glass, quartz, sand, or vermiculite; calcium carbonate (e.g. Bora-Bora sand or Rose de Brignoles sand) or magnesium carbonate; sodium chloride; pumice stone; amorphous silica; diamond; ceramics, and (2) organic particles such as: fruit stones, in particular apricot stones, e.g. Scrubami® apricot; wood cellulose, e.g. ground bamboo stem; coconut shell, e.g. coconut exfoliator; polyamides, in particular Nylon-6; sugars; plastic microbeads, e.g. polyethylenes or polypropylenes; ground walnut; ground apricot seed; ground shells, and (3) mixed particles associating organic and inorganic compounds, and particles coated in the above compounds. The exfoliating agents may be in the form of microbeads of less than five millimeters in its largest dimension that have an exfoliating effect.

In one embodiment, the therapeutic agent is incorporated into capsules or other slow release vehicles in the composition that allow the chemical or agent to be slowly released into the dermis. Capsules or vehicles that encapsulate the therapeutic agent can include, but are not limited to, liposomes, non-ionic liposomes, niosomes, novasome I, erythromycin-Zn complex, microspheres, nanoparticles, solid lipid nanoparticles, and nanoemulsions.

The dosage applied to each nipple-areola complex on a female or male patient will be specific for the different therapeutic agents disclosed herein. One of ordinary skill may use standard practices and testing to determine an acceptable dosage. In one embodiment, the dosage applied on a nipple-areola complex is between 0.1-15, 10-15, 5-20, 10-20, 0.1-5.0, 0.2-0.8, 0.4-5.0, 0.4-4.0, 0.4-3.0, 0.4-2.0, 0.4-1.0, 0.4-0.8, 0.6-5.0, 0.6-4.0, 0.6-3.0, 0.6-1.0, 1.0-5.0, 1.0-4.0, 1.0-3.0, 1.0-2.0, 1.5-5.0, 1.5-4.0, 1.5-3.0, 1.5-2.0, 1.5-3.5, 0.1-2.0, 0.2-2.0, 0.3-2.0, 0.5-2.0, 0.6-2.0, 0.7-2.0, 0.8-2.0, 0.9-2.0, 1.1-2.0, 1.2-2.0, 1.3-2.0, 1.4-2.0, 1.5-2.0, 1.6-2.0, 1.7-2.0, 1.8-2.0, or 1.9-2.0 mg/cm$^2$ of therapeutic agent. In one embodiment, the therapeutic agent is phenylephrine, oxymetazoline or synephrine and the dosage applied on a nipple-areola complex is between 0.05-5.0, 0.1-5.0, 0.4-5.0, 0.4-4.0, 0.4-3.0, 0.4-2.0, 0.4-1.0, 0.4-0.8, 0.6-5.0, 0.6-4.0, 0.6-3.0, 0.6-1.0, 1.0-5.0, 1.0-4.0, 1.0-3.0, 1.0-2.0, 1.5-5.0, 1.5-4.0, 1.5-3.0, 1.5-2.0, 1.5-3.5, 0.1-2.0, 0.2-2.0, 0.3-2.0, 0.5-2.0, 0.6-2.0, 0.7-2.0, 0.8-2.0, 0.9-2.0, 1.1-2.0, 1.2-2.0, 1.3-2.0, 1.4-2.0, 1.5-2.0, 1.6-2.0, 1.7-2.0, 1.8-2.0, or 1.9-2.0 mg/cm$^2$. In one embodiment the dosage of the therapeutic agent is 0.1-2.0, 0.5-2.0, 1.0-2.0, 0.1-1.0, 0.2-1.0, 0.3-1.0, 0.4-1.0, 0.5-1.0, 0.6-1.0, 0.7-1.0, 0.8-1.0, 0.9-1.0, 0.1-0.9, 0.2-0.9, 0.2-0.8, 0.2-0.7, 0.3-0.9, 0.3-0.8, 0.3-0.7, 0.4-0.9, 0.4-0.8, 0.5-0.9, 0.5-0.8, 0.5-0.7, or about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, or 2.0 mg/cm$^2$. In one embodiment when the therapeutic agent is phenylephrine, methoxamine or oxymetazoline, the dosage of the therapeutic agent is 0.1-2.0, 0.5-2.0, 1.0-2.0, 0.1-1.0, 0.2-1.0, 0.3-1.0, 0.4-1.0, 0.5-1.0, 0.6-1.0, 0.7-1.0, 0.8-1.0, 0.9-1.0, 0.1-0.9, 0.2-0.9, 0.2-0.8, 0.2-0.7, 0.3-0.9, 0.3-0.8, 0.3-0.7, 0.4-0.9, 0.4-0.8, 0.5-0.9, 0.5-0.8, 0.5-0.7, or about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, or 2.0 mg/cm$^2$. In another embodiment the therapeutic agent is phenylephrine HCl and the dosage is 0.1-2.0, 0.5-2.0, 1.0-2.0, 0.1-1.0, 0.2-1.0, 0.3-1.0, 0.4-1.0, 0.5-1.0, 0.6-1.0, 0.7-1.0, 0.8-1.0, 0.9-1.0, 0.1-0.9, 0.2-0.9, 0.2-0.8, 0.2-0.7, 0.3-0.9, 0.3-0.8, 0.3-0.7, 0.4-0.9, 0.4-0.8, 0.5-0.9, 0.5-0.8, 0.5-0.7, or about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, or 2.0 mg/cm$^2$. Under this dosage measurement, a smaller dimension of the nipple-areola complex will result in a lower total dose.

As measured by in vitro release testing (IVRT), the dosage that penetrates the stratum may be about 90, 80, 70, 60, 50, 40 or 30% of the dosage topically applied. In one embodiment, the dosage that penetrates the stratum is between 0.1-1.0, 0.2-1.0, 0.3-0.9, 0.4-0.8, 0.5-1.0, 0.6-1.1, 0.01-1.0, or 0.01-0.1 mg/cm$^2$, or is approximately 0.1, 0.2, 0.3, 0.4, 0.5, 0.6, 0.7, 0.8 or 0.9 mg/cm$^2$.

The therapeutic agent can be applied in a transdermal patch of any appropriate size and formulation that allows for administration of a therapeutically effective amount of the therapeutic agent. In one embodiment, the nipple-areola complex may be measured and a circle of the appropriate size of a transdermal patch applied to encompass the entire nipple-areola surface. In certain embodiments, the circular transdermal patches are 8, 12 and 16 cm in diameter. In other embodiments, the circular transdermal patch is 5, 6, 7, 8, 9, 10, 11, 12, 13, 14, 15, 16, 17, 18, 19, or 20 cm in diameter, or is a size ranging from 5-10, 6-11, 7-12, 8-13, 9-14, 10-15, 11-16, 12-17, 13-18, 14-19, or 15-20 cm in diameter. Based on a transdermal patch or occlusive covering of a therapeutic composition of 8 cm in diameter, a total dosage of 5 mg may be applied in one embodiment. Similarly, a patch 12 cm in diameter may apply a total dose of 7.5 mg and a patch of 16 cm may apply a total dose of 10 mg.

In one embodiment, the therapeutic agent is present in the composition for topical administration at a concentration of 0.025-1.0, 0.05-1.0, 0.025-2.0, 0.05-2.0, 0.05-3.0, 0.05-4.0, 0.5-1.0, 0.5-2.0, 0.5-3.0, 0.1-40.0, 0.1-35.0, 0.1-25.0, 0.1-10.0, 0.1-15.0, 0.1-5.0, 1.0-25.0, 1.0-10.0, 1.0-15.0, 1.0-5.0, 5.0-25.0, 5.0-10.0, 5.0-15.0, 5.0-10, 5.0-15.0, 5.0-20.0, 10.0-20.0, 20.0-30.0, 25.0-30.0, 30.0-40.0, 10.0-40.0, or 35.0-40.0% by weight, or approximately 1.0, 2.0, 3.0, 4.0, 5.0, 6.0, 7.0, 8.0, 9.0, 10.0, 11.0, 12.0, 13.0, 14.0, 15.0, 16.0, 17.0, 18.0, 19.0, 20.0, 21.0, 22.0, 23.0, 24.0, 25.0, 26.0, 27.0, 28.0, 29.0, 30.0, 31.0, 32.0, 33.0, 34.0, 35.0, 36.0, 37.0, 38.0, 39.0, or 40% by weight. In one embodiment, the therapeutic agent is phenylephrine, synephrine or a pharmaceutically acceptable salt or hydrate thereof and is in a composition at a concentration of 5% to 10% or 10% to 30% therapeutic agent by total weight of the composition. In one embodiment, the composition comprises an A1AR agonist in a concentration of about 0.25, 0.33, 0.5, 1.0, 2.0 or 2.5% by weight. In one embodiment, the composition comprises methoxamine or oxymetazoline (such as oxymetazoline HCl) in a concentration of about 0.025-1.0, 0.05-1.0, 0.025-2.0, 0.05-3.0, 0.05-5.0, 0.05-4.0, 0.1-5.0 or 0.5-2.0% by weight or in a concentration of about 0.025, 0.05, 0.25, 0.33, 0.5, 1.0, 2.0, 2.5, 3.0, 3.5, 4.0, 4.5, or 5.0% by weight. In one embodiment, the therapeutic agent is midodrine and is present in the composition at a concentration of 0.025-5.0, 0.05-5.0, 0.1-5.0, 0.2-5.0, 0.025-2.0, 0.05-2.0, 0.2-2.0 or 0.1-3.0% by weight. As is readily understood by the person of ordinary skill in the field, the concentration of therapeutic agent in a composition can vary depending on the particular therapeutic agent used and the efficacy of the composition containing it to deliver the agent through the dermis.

In one embodiment, the method is to treat female sexual dysfunction, preferably female sexual arousal disorder (FSAD), female sexual interest/arousal disorder (FSIAD), female orgasmic disorder (FOD) or female hypoactive sexual desire disorder (FHSDD), by applying a therapeutically effective amount of a composition comprising an A1AR agonist, such as phenylephrine, topically to a nipple-areola complex of a female subject in need of such treatment, such as a premenopausal woman, in an amount of 0.2-0.8 mg/cm$^2$ A1AR agonist per surface area of the nipple-areola complex. In another embodiment, the method is to treat treating female sexual dysfunction, preferably female sexual arousal disorder (FSAD), female sexual interest/arousal disorder (FSIAD), female orgasmic disorder (FOD) or female hypoactive sexual desire disorder (FHSDD), by applying a therapeutically effective amount of a composition comprising an A1AR agonist, such as phenylephrine, topically to a nipple-areola complex of a female subject in need of such treatment, such as a postmenopausal woman, in an amount of 0.2-0.8 mg/cm$^2$ A1AR agonist per surface area of the nipple-areola complex. In a further embodiment, the method is to reduce or alleviate a symptom of female sexual dysfunction, such as (1) absent/reduced interest in sexual activity; (2) absent/reduced sexual/erotic thoughts or fantasies; (3) no/reduced initiation of sexual activity, and typically unreceptive to a partner's attempts to initiate; (4) absent/reduced sexual excitement/pleasure during sexual activity in almost all or all sexual encounters; (5) absent/reduced sexual interest/arousal in response to any internal or external sexual/erotic cues; or (6) absent/reduced genital or nongenital sensations during sexual activity in almost all or all sexual encounters, the method comprising applying a therapeutically effective amount of a composition comprising an A1AR agonist, such as phenylephrine, in a dosage of 0.2-0.8 mg/cm$^2$, topically to a nipple-areola complex of a female subject in need of such treatment. In yet a further embodiment, the method is for causing erection of nipples, increasing nipple sensitivity, and/or increasing oxytocin release related to sexual activity in a female subject, such as a premenopausal or postmenopausal woman, comprising applying an effective amount of a composition comprising an A1AR agonist, such as phenylephrine, topically to a nipple-areola complex of the female subject in an amount of 0.2-0.8 mg/cm$^2$.

The pH of the formulation will be determined following procedures known in the art to provide for stability of the therapeutic agent and allow for skin penetration of the agent. Phenylephrine, for example, may be formulated at a pH of less than 6, particularly if it is concentrated at 10% or more by weight of the formulation. In one embodiment, phenylephrine is formulated at 10% by weight or higher in a liquid solution that does not contain ethanol and has a pH of less than 6, preferably 5.5 or between 4.9 and 5.5, 4.9 and 5.6, 4.9 and 5.7, 4.9 and 5.8, 4.9 and 5.9, 5.0 and 5.8, 5.0 and 5.9, 5.1 and 5.8, 5.1 and 5.7, 5.2 and 5.8, 5.3 and 5.8, 5.3 and 5.7, or 5.4 and 5.6.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of elements that do not materially affect the basic and novel or functional characteristic(s) of that embodiment.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Measurement of the strength of nipple smooth muscle contraction can be performed, if necessary, via myograph adapted for that purpose. Examples are described in, e.g., Zeveke & Gladysheva, Bull. Exp. Biol. Med. 71: 102-105 (1971) and Hellmann, J. Physiol. 169: 603-620 (1963). Measurement of nipple sensitivity can be performed, if necessary, via Semmes-Weinstein monofilament test adapted for that purpose. Other methods for measuring nipple sensitivity (i.e., sensibility) have been described. Examples are described in, e.g., Mofid, Dellon, Elias & Nahabedian, Plast Reconstr Surg. 109(7):2283-2288 (2002).

Efficacy of treatment for FSD and enhancement of sexual satisfaction can be determined by monitoring the number of satisfying sexual events (SSE) in a given experimental period. For example, a questionnaire may be administered by a clinician asking the number of SSEs a patient has experienced in a given four-week period. A treatment can thus be applied for another four-week period and the questionnaire can be re-assessed at the end of the treatment. An increase in SSE from baseline can then be evaluated, for example, in a statistically significantly large cohort. As but one example, an average increase from 6 to 6.7 SSEs would show efficacy of a treatment. Similarly, secondary endpoints could include questionnaires assessing sexual satisfaction, e.g., change from baseline to end-of-study in arousal domain score, female sexual function index, satisfaction with arousal, desire domain from female sexual function index, satisfaction with desire, quality of relationship with partner, and a female sexual distress scale. Other established metrics to determine treatment efficacy for FSD can also be used, and they include, for example, FSFI (female sexual function index), SAL (Sexual Activity Log), SAR (Sexual Activity Record), FSDS (Female Sexual Distress Scale), and the FSDS-R (Female Sexual Distress Scale Revised).

Other parameters to measure or quantify sexual arousal in females include arousal domain score from female sexual function index, satisfaction with arousal, desire domain from female sexual function index, satisfaction with desire as measured, quality of relationship with partner, change in hormone levels such as oxytocin, length of time of nipple erection. A treatment is considered effective if any one or a combination of these parameters is increased as compared to a reference level that is measured in the absence of the treatment.

Agents that promote the contraction of smooth muscle can optionally be administered by iontophoresis, which uses an electric field to drive the passage of ionic agents or drugs into the skin. As but one example, iontophoresis has been used to deliver agents such as phenylephrine to the skin to stimulate smooth muscle contraction. See, e.g., Siepmann et al., Neurology Apr. 25, 2012; 78 (Meeting Abstracts 1): P05.197. Thus, in one embodiment, a device can incorporate an iontophoresis device, which can dispense the A1AR agonist or other agent and/or be used for transdermal delivery of the agent(s). The iontophoresis device can comprise one or more metal contacts. Optionally, the iontophoresis device can comprise one or more compartments for containing the A1AR agonist or other agent(s).

Penetration enhancement of an A1AR agonist across the stratum corneum can be achieved by applying an electric field gradient across the skin. This iontophoresis method is well established in the literature. See Nitin Dixit, Vikas Bali, Sanjula Baboota, Alka Ahuja and Javed Ali (2007), "Iontophoresis—An Approach for Controlled Drug Delivery: A Review", Current Drug Delivery, 4, 1-10. For example, phenylephrine hydrochloride, a selective alpha 1 adrenergic receptor agonist, has been successfully iontophorised across the stratum corneum and delivered to the arrector pili muscle producing piloerection on the forearm. See T. Siepmann, C. H. Gibbons, B. M. Illigens, J. A. Lafo, C. M. Brown, and R. Freeman (2012), "Quantitative Pilomotor Axon-Reflex Test—A Novel Test of Pilomotor Function", Archives of Neurology (2012), 69(11), 1488-1492. The advantage of using iontophoresis is that the concentrations of active agent required to penetrate the stratum corneum are typically much lower than those needed with other topical formulations. For example, a 1% w/v concentration of phenylephrine hydrochloride can activate the piloerection on the forearm when iontophoresis in used. See T. Siepmann, Archives of Neurology (2012), supra.

In one embodiment of the present invention, a solution of therapeutic agent, for example, an A1AR agonist, is placed in an iontophoresis patch specifically designed for the nipple areola complex. Devices such as these are well known in the art. See, e.g., U.S. Pat. No. 8,442,629 B2 (Suzuki); U.S. Pat. No. 4,968,297 A (Jacobsen); U.S. Pat. No. 8,362,027 B2 (Inagi); U.S. Pat. No. 4,419,092 A (Jacobsen); U.S. Pat. No. 8,423,131 B2 (Mir Imran); U.S. Pat. No. 5,087,242 A (Tomasz); U.S. Pat. No. 5,248,295 A (Jacobsen). It is important to note that the net charge of the drug must be matched with the like charged terminal of the iontophoretic device. For example, if a solution of phenylephrine hydrochloride is used, the solution should be placed on the positively charged electrode of the iontophoresis patch. During iontophoresis, an electric field drives the charged drug molecules across the stratum corneum. This method of delivering the A1AR agonist by applying the A1AR agonist on or in an iotophoresis patch is believed to be useful with any of the inventive methods of use disclosed herein, as is apparent to one of ordinary skill in the art.

In one embodiment of the invention, electroporation is used to enhance the permeability of the stratus corneum. During electroporation, an electric current is applied to the skin, creating pores in the stratum corneum that facilitate diffusion of the drug molecules. The drug may diffuse across the stratum corneum by static diffusion. In an embodiment, electroporation is combined with iontophoresis, and the drug is further driven through the stratus corneum by an electric field. It should be understood that electroporation may be used to enhance permeability of any of the therapeutic compositions disclosed herein, with or without the added use of iontophoresis.

In one embodiment of the invention, a voltage of about 30 V to about 500 V are applied to the skin for electroporation. In an embodiment, the voltage is pulsed for a short duration. In some embodiments, the short duration is in a range of greater than 0 ms to about 300 ms.

Electrical Stimulation

In one embodiment of the invention, the smooth muscle can be contracted via electrical stimulation to at least a portion of the nipple-areola complex of the breast. The electrical stimulation can be controlled, e.g., by a unit. Examples of applying electrical forces to contract the smooth muscles are described in, for example, US Patent Application Pub. US2013/0199348 published on Aug. 8, 2013, titled Pilomotor Effect Stimulating Device and Method. In some embodiments, the voltage or amplitude of the signal applied can be in the range of 35 to 75 volts, 25 to 50 volts, 10 to 30 volts or other suitable ranges to reach the threshold for muscle contraction. The current applied by a device as disclosed herein can, in some embodiments, preferably be in the microamps to avoid electrocution of the user. A frequency of 10 KHz to 15 KHz can be applied, or a lower or higher frequency. In some embodiments, the pulse length applied will be from 1 to 50 milliseconds, 1 to 100 milliseconds, or other suitable lengths to contract smooth muscle of at least a portion of the nipple-areola complex or any other pilomotor effective amount of current. In some embodiments, a control unit will automatically pulse the electrical stimulation at random intervals that are enough to keep the smooth muscle relatively contracted. In other embodiments, the pulses will be spaced out enough to allow the smooth muscle to relax in between pulses.

In one embodiment, the electrical stimulation device can be built into a bra. A female subject can wear the bra with the electrical stimulation device and promote stimulation by turning on the device.

It should be noted that combinations of the above methods and therapeutic agents can be used to promote the contraction of the smooth muscle and achieve the desired therapeutic results and enhancement of sexual satisfaction.

The various methods and techniques described above provide a number of ways to carry out the invention. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some embodiments specifically include one, another, or several features, while others specifically exclude one, another, or several features, while still others mitigate a particular feature by inclusion of one, another, or several advantageous features.

All patents, patent applications, publications of patent applications, and other published material, such as articles and books referenced herein are hereby incorporated herein by this reference in their entireties. Should there be any inconsistency or conflict between the description, definition, and/or the use of a term associated with any of the incorporated material and that associated with the present document, the description, definition, and/or the use of the term in the present document shall prevail.

EXAMPLES

The following examples illustrate some embodiments and aspects of the invention. It will be apparent to those skilled in the relevant art that various modifications, additions, substitutions, and the like can be performed without altering the spirit or scope of the invention, and such modifications and variations are encompassed within the scope of the invention as defined in the claims which follow. The technology disclosed herein is further illustrated by the following examples which in no way should be construed as being further limiting.

Example 1

Transdermal Delivery of 10% Phenylephrine Solution

Transdermal penetration of a particular formulation can be assessed with in vitro release testing (IVRT) using a Franz cell. See Bartosova and Bajagar, "Transdermal Drug Delivery In Vitro Using Diffusion Cells," Current Medicinal Chemistry, 2012, 19, 4671-4677.

In order to determine the dermal absorption and bioavailability of topically applied 10% Phenylephrine Hydrochloride solution, we used an IVRT experimental setup with both skin excised from pig ears and a synthetic skin model (Maine Manufacturing, LLC, Maine, USA). In both models (see table below), the maximal skin absorption in 24 hours did not exceed 83%.

In the example, the following data was obtained from a Franz cell diffusion experiment using excised pigskin barrier. A 50 microliter aliquot of a phenylephrine solution was allowed to penetrate through 9 mm diameter sample of pigskin into a 5 mL reservoir of phosphate buffered saline. Phenylephrine concentration was determined in the reservoir by measuring the optical absorbance at 214 nm at time points subsequent to the application of the formulation. In the following example the test solution was 10% (w/w) phenylephrine, 10% (w/w) Dimethyl Isosorbide, and 80% (w/w) ethanol. From the data below, it can be concluded that the formulation can be deemed "successful" because 82% of the applied drug penetrated the pigskin membrane in 3 hours. The experiment was run in triplicate. The average of all three data is shown. It is envisioned that additional studies may be undertaken with other models of in vitro release testing or with variations of the same model to compare with the data reported below.

TABLE 1

IVRT skin penetration model (pig skin) of 10% Phenylephrine HCl solution.

| Time (h) | Penetration (%) | | | |
|---|---|---|---|---|
| | Sample 1 | Sample 2 | Sample 3 | Average |
| 1 | 32.3% | 2.1% | 0.7% | 11.7% |
| 2 | 80.6% | 89.0% | 13.6% | 61.1% |
| 3 | 78.9% | 87.5% | 81.9% | 82.8% |
| 4 | 78.6% | 83.4% | 81.1% | 81.0% |
| 5 | 78.5% | 86.0% | 81.3% | 81.9% |
| 24 | 81.3% | 83.1% | 80.3% | 81.6% |

Therefore, if a subject is to apply 0.1 mL of the drug solution and not remove it for a period of 24 hours (which is unlikely to occur), she will experience an average absorption of 8.3 mg of PhenylephrineHCl per nipple-areola complex or 16.6 mg total absorption over 24 hours. In comparison, in the United States, Over-the-Counter (OTC) Sudafed® phenylephrine contains 10 mg phenylephrine hydrochloride oral tablets indicated for administration of 10 mg to 20 mg every 4 hours. The oral dosage is approximately 40% systemically bioavailable. Assuming one Sudafed® PE phenylephrine tablet every 4 hours or 60 mg per day, the total dosage will be 24 mg. The dosage proposed in the present study will result in approximately 45% less systemic PhenylephrineHCl exposure compared to the oral OTC drug.

In addition, while the percent of ocular absorption has not been determined, the 10% ophthalmic solution approved by the US FDA was found safe based on assuming complete absorption of 21 mg PhenylephrineHCl per day, which is also higher than the absorption at the dosage disclosed herein for the treatment of FSD.

Finally, it should be noted that systemic bioavailability of topically applied PhenylephrineHCl is likely to be far lower than the maximal estimated amount due to the local vasoconstriction effect of the drug; hence, the reduced systemic absorption.

Example 2

A study of the blood pressure and heart rate of five patients receiving topical application on the nipple-areola complex was made. The composition applied was 0.1 mL of a 10% phenylephrine solution for a total dosage of 10 mg phenylephrine HCl. Blood pressure and heart rate were measured at baseline (T=0), after 15 minutes and 30 minutes. No significant change in blood pressure or heart rate was detected in any of the subjects.

This data supports the safety of the topically applied dosage (~15-20 mg) of phenylephrine. The applied dosage does not provide for an increase in systemic heart rate or blood pressure.

TABLE 2

0.1 mL 10% PHCl

| Subject Nr. | BP (T = 0) | BP (T = 15) | BP (T = 30) | HR (T = 0) | HR (T = 15) | HR (T = 30) |
|---|---|---|---|---|---|---|
| 1 | 115/80 | 112/76 | 117/75 | 82 | 69 | 74 |
| 2 | 119/78 | 122/77 | 122/78 | 81 | 77 | 80 |
| 3 | 116/76 | 117/72 | 128/77 | 74 | 75 | 68 |
| 4 | 116/74 | 120/72 | 116/68 | 51 | 53 | 58 |
| 5 | 100/67 | 99/67 | 97/63 | 63 | 68 | 69 |

Example 3

A pilot study was conducted to assess the dosage of topical phenylephrine solution required to elicit nipple erection and sensitivity. Five subjects ages 18-70 participated in the study. Two subjects were post-menopausal and the reminder three were pre-menopausal. Subjects were not hypertensive, pregnant or breastfeeding. Three formulations were used: Formula A: 0% topical phenylephrine hydrochloride solution; Formula B: 5% topical phenylephrine hydrochloride solution; Formula C: 10% topical phenylephrine hydrochloride solution.

The study was conducted over 3 days. On day 1, subjects were instructed to apply on the left nipple Formula A and on the right nipple Formula B. On day 2, subjects were instructed to apply on the left nipple Formula A and on the right nipple Formula C. On day 3, subjects were instructed to apply on the left nipple Formula B and on the right nipple Formula C. 0.1 mL of each formula was applied with a cotton swab to the nipple areole complex. Table 3 summarizes the finding from this study. The 10% topical phenylephrine solution (Formula C) elicited a clinical response in all subjects while the 5% and placebo formulations (Formula A and B) failed to elicit a response. With the 10% topical phenylephrine solution, response in nipple erection and sensitivity was obtained in less than 30 minutes and lasted for 3-4 hours.

TABLE 3

| | Day 1 | | Day 2 | | Day 3 | |
|---|---|---|---|---|---|---|
| Subject Nr. | Formula A | Formula B | Formula A | Formula C | Formula B | Formula C |
| 001 | NR | NR | NR | R | NR | R |
| 002 | NR | NR | NR | R | NR | R |
| 003 | NR | NR | NR | R | NR | R |
| 004 | NR | NR | NR | R | NR | R |
| 005 | NR | NR | NR | R | NR | R |

R = Response i.e., nipple erection
NR = No Response

Example 4

An additional pilot study was conducted to assess the safety and efficacy of topical phenylephrine applied to the nipple-areole complex for the treatment of female sexual dysfunction. Nine women subjects ages 18-70 participated in the study. Two subjects were post-menopausal and the remaining seven were pre-menopausal. Subjects were not suffering from clinical depression, hypertension, pregnant, breastfeeding or currently taking testosterone, SSRIs, or other antidepressants. 0.1 mL of 10% topical phenylephrine hydrochloride solution was applied with a cotton swab to each nipple areole complex (a total dosage of 20 mg was applied topically). Subjects were instructed to apply the solution approximately 1 hour before sexual activity. The duration of the study was for a period of one week. The number of Satisfying Sexual Events (SSE) determined by a Sexual Activity Record (SAR) was recorded. In addition, a modified Female Sexual Function Index (FSFI) desire domain questionnaire was administered. Table 4 summarizes the change in SSEs from baseline as well as Adverse Events (AE). All subjects reported increased nipple sensitivity within 30 minutes after the application of the topical phenylephrine solution. The nipples remained sensitive up to 3 to 4 hours. In one subject, with initial slightly painful nipple erection, the sensitivity persisted for approximately 8 hours. Seven subjects reported significant change in the number of SSEs from baseline. Subjects reporting increase in the number of SSEs also reported increased desire possibly attributed to the hypothesized mechanism of action of oxytocin release as a result of nipple erection.

TABLE 4

| Subject Nr. | Number of SSE (baseline) | Number of SSE (1 week) |
| --- | --- | --- |
| 001 | 1 | 3 |
| 002 | 0 | 2 |
| 003 | 0 | 1 |
| 004 | 2 | 4 |
| 005 | 1 | 3 |
| 006 | 2 | 2 |
| 007 | 1 | 1 |
| 008 | 3 | 6 |
| 009 | 2 | 3 |

Example 5: Protocols for Clinical Studies

Primary outcome measures: Number of satisfying sexual events (SSE) determined from Sexual Activity Record (SAR).

Secondary outcome measures: Female Sexual Function Index (FSFI);

Female Sexual Distress Scale, Revised (FSDS-R); Sexual Quality of Life-Female (SQOL-F).

Efficacy Parameters

During the first site visit, week 4 site visit and week 8 site visit, the primary investigator (PI) will instruct the subject in the use of the sexual activity record (SAR). In addition, during week 4 site visit and week 8 site final visit, the PI will administer standardized patient reported outcomes (PROs) of FSD.

PROs:

Sexual Activity Record (SAR): The SAR was developed to measure the frequency of successful and satisfactory sexual events as a primary end point in clinical trials of sexual dysfunction. The SAR is a brief form that is completed after the respondent engages in sexual activity. Its seven items assess the respondent's experience of the most recent sexual encounter in the areas of sexual arousal, orgasm, and overall satisfaction with sexual arousal. Respondents indicate whether sexual events include self-stimulation, partnered sexual activity, or a combination of both.

Female Sexual Function Index (FSFI): The FSFI is a 19-item multidimensional self-report instrument (Table 5) used to assess women's sexual function in six domains: desire, arousal, lubrication, orgasm, satisfaction, and pain. The instrument yields scores for each of these six domains as well as a total score. The FSFI has demonstrated good test-retest reliability (a=0.79-0.88). Rosen et al., 2000, "The Female Sexual Function Index (FSFI): A multidimensional self-report instrument for the assessment of female sexual function," Journal of Sex and Marital Therapy, 26, 191-208; Wiegel, M., Meston, C., & Rosen, R., 2005, "The Female Sexual Function Index: Cross-validation and development of clinical cut-off scores," Journal of Sex & Marital Therapy, 31, 1-20.

TABLE 5

| FSFI | |
| --- | --- |
| Question | Response Options |
| 1. Over the past 4 weeks, how often did you feel sexual desire or interest? | 5 = Almost always or always<br>4 = Most times (more than half the time)<br>3 = Sometimes (about half the time)<br>2 = A few times (less than half the time)<br>1 = Almost never or never |
| 2. Over the past 4 weeks, how would you rate your level (degree) of sexual desire or interest? | 5 = Very high<br>4 = High<br>3 = Moderate<br>2 = Low<br>1 = Very low or none at all |
| 3. Over the past 4 weeks, how often did you feel sexually aroused ("turned on") during sexual activity or intercourse? | 0 = No sexual activity<br>5 = Almost always or always<br>4 = Most times (more than half the time)<br>3 = Sometimes (about half the time)<br>2 = A few times (less than half the time)<br>1 = Almost never or never |
| 4. Over the past 4 weeks, how would you rate your level of sexual arousal ("turn on") during sexual activity or intercourse? | 0 = No sexual activity<br>5 = Very high<br>4 = High<br>3 = Moderate<br>2 = Low<br>1 = Very low or none at all |
| 5. Over the past 4 weeks, how confident were you about becoming sexually aroused during sexual activity or intercourse? | 0 = No sexual activity<br>5 = Very high confidence<br>4 = High confidence<br>3 = Moderate confidence<br>2 = Low confidence<br>1 = Very low or no confidence |

TABLE 5-continued

FSFI

| Question | Response Options |
|---|---|
| 6. Over the past 4 weeks, how often have you been satisfied with your arousal (excitement) during sexual activity or intercourse? | 0 = No sexual activity<br>5 = Almost always or always<br>4 = Most times (more than half the time)<br>3 = Sometimes (about half the time)<br>2 = A few times (less than half the time)<br>1 = Almost never or never |
| 7. Over the past 4 weeks, how often did you become lubricated ("wet") during sexual activity or intercourse? | 0 = No sexual activity<br>5 = Almost always or always<br>4 = Most times (more than half the time)<br>3 = Sometimes (about half the time)<br>2 = A few times (less than half the time)<br>1 = Almost never or never |
| 8. Over the past 4 weeks, how difficult was it to become lubricated ("wet") during sexual activity or intercourse? | 0 = No sexual activity<br>1 = Extremely difficult or impossible<br>2 = Very difficult<br>3 = Difficult<br>4 = Slightly difficult<br>5 = Not difficult |
| 9. Over the past 4 weeks, how often did you maintain your lubrication ("wetness") until completion of sexual activity or intercourse? | 0 = No sexual activity<br>5 = Almost always or always<br>4 = Most times (more than half the time)<br>3 = Sometimes (about half the time)<br>2 = A few times (less than half the time)<br>1 = Almost never or never |
| 10. Over the past 4 weeks, how difficult was it to maintain your lubrication ("wetness") until completion of sexual activity or intercourse? | 0 = No sexual activity<br>1 = Extremely difficult or impossible<br>2 = Very difficult<br>3 = Difficult<br>4 = Slightly difficult<br>5 = Not difficult |
| 11. Over the past 4 weeks, when you had sexual stimulation or intercourse, how often did you reach orgasm (climax)? | 0 = No sexual activity<br>5 = Almost always or always<br>4 = Most times (more than half the time)<br>3 = Sometimes (about half the time)<br>2 = A few times (less than half the time)<br>1 = Almost never or never |
| 12. Over the past 4 weeks, when you had sexual stimulation or intercourse, how difficult was it for you to reach orgasm (climax)? | 0 = No sexual activity<br>1 = Extremely difficult or impossible<br>2 = Very difficult<br>3 = Difficult<br>4 = Slightly difficult<br>5 = Not difficult |
| 13. Over the past 4 weeks, how satisfied were you with your ability to reach orgasm (climax) during sexual activity or intercourse? | 0 = No sexual activity<br>5 = Very satisfied<br>4 = Moderately satisfied<br>3 = About equally satisfied and dissatisfied<br>2 = Moderately dissatisfied<br>1 = Very dissatisfied |
| 14. Over the past 4 weeks, how satisfied have you been with the amount of emotional closeness during sexual activity between you and your partner? | 0 = No sexual activity<br>5 = Very satisfied<br>4 = Moderately satisfied<br>3 = About equally satisfied and dissatisfied<br>2 = Moderately dissatisfied<br>1 = Very dissatisfied |
| 15. Over the past 4 weeks, how satisfied have you been with your sexual relationship with your partner? | 5 = Very satisfied<br>4 = Moderately satisfied<br>3 = About equally satisfied and dissatisfied<br>2 = Moderately dissatisfied<br>1 = Very dissatisfied |
| 16. Over the past 4 weeks, how satisfied have you been with your overall sexual life? | 5 = Very satisfied<br>4 = Moderately satisfied<br>3 = About equally satisfied and dissatisfied<br>2 = Moderately dissatisfied<br>1 = Very dissatisfied |
| 17. Over the past 4 weeks, how often did you experience discomfort or pain during vaginal penetration? | 0 = Did not attempt intercourse<br>1 = Almost always or always<br>2 = Most times (more than half the time)<br>3 = Sometimes (about half the time)<br>4 = A few times (less than half the time)<br>5 = Almost never or never |
| 18. Over the past 4 weeks, how often did you experience discomfort or pain following vaginal penetration? | 0 = Did not attempt intercourse<br>1 = Almost always or always<br>2 = Most times (more than half the time)<br>3 = Sometimes (about half the time)<br>4 = A few times (less than half the time)<br>5 = Almost never or never |

TABLE 5-continued

| | FSFI |
|---|---|
| Question | Response Options |
| 19. Over the past 4 weeks, how would you rate your level (degree) of discomfort or pain during or following vaginal penetration? | 0 = Did not attempt intercourse<br>1 = Very high<br>2 = High<br>3 = Moderate<br>4 = Low<br>= Very low or none at all |

The individual domain scores and full scale (overall) score of the FSFI can be derived from the computational formula outlined in Table 4. For individual domain scores, add the scores of the individual items that comprise the domain and multiply the sum by the domain factor (see below). Add the six domain scores to obtain the full scale score. It should be noted that within the individual domains, a domain score of zero indicates that the subject reported having no sexual activity during the past month. Subject scores can be entered in the right-hand column. Significant positive changes in score reflect efficacy of the methods of treatment described herein.

TABLE 6

| Domain | Questions | Score Range | Factor | Minimum Score | Maximum Score | Score |
|---|---|---|---|---|---|---|
| Desire | 1, 2 | 1-5 | 0.6 | 1.2 | 6.0 | |
| Arousal | 3, 4, 5, 6 | 0-5 | 0.3 | 0 | 6.0 | |
| Lubrication | 7, 8, 9, 10 | 0-5 | 0.3 | 0 | 6.0 | |
| Orgasm | 11, 12, 13 | 0-5 | 0.4 | 0 | 6.0 | |
| Satisfaction | 14, 15, 16 | 0 (or 1)-5 | 0.4 | 0.8 | 6.0 | |
| Pain | 17, 18, 19 | 0-5 | 0.4 | 0 | 6.0 | |
| | Full Scale Score Range | | | 2.0 | 36.0 | |

Female Sexual Distress Scale-Revised (FSDS-R): The FSDS (original version) is a self-report questionnaire developed to measure sexually related personal distress in women. Response choices are "never," "rarely," "occasionally," "frequently," and "always." The questionnaire is scored by summing the item responses (scaled such that "never" equals 0 and "always" equals 4). The FSDS-R differs from the FSDS in that it includes one additional question that asks women to rate distress related to low sexual desire. This modification is more consistent with diagnosis of HSDD. Significant improvement in score indicates therapeutic efficacy.

Sexual Quality of Life—Female (SQoL-F): The SQoL-F is an 18-item questionnaire developed to assess the sexual quality of life women, specifically to assess sexual confidence, emotional well-being and relationship issues. The instrument has been validated for use in a broad range of women with Female Sexual Arousal Disorder and Hypoactive Sexual Desire Disorder. Significant improvement in score indicates therapeutic efficacy.

Example 6

A pilot study was conducted to assess the optimal pH of topical phenylephrine solution required to elicit smooth muscle contraction on the skin. A series of 10% phenylephrine solutions were prepared in phosphate buffer solutions of varied pH. pH 4.6, 4.8, 5.0, 5.2, 5.4, 5.6, 5.8, 6.0, 6.2, 6.4, and 6.6 were used. Areas of skin on the subjects forearm were marked with a surgical pen. 50 microliter of each solution were applied to the marked area of skin and allowed to dry. After one hour the sites of application were visually inspected for the appearance of the pilomotor effect (i.e., "goose bumps"). The results are summarized in the table below:

TABLE 7

| pH of 10% Phenylephrine Solution | Results after 1 hour |
|---|---|
| 4.6 | None |
| 4.8 | Slight |
| 5.0 | Strong |
| 5.2 | Strong |
| 5.4 | Strong |
| 5.6 | Slight |
| 5.8 | Slight |
| 6.0 | None |
| 6.2 | None |
| 6.4 | None |
| 6.6 | None |

Example 7

Oxymetazoline HCl 0.1%, 0.2%, 0.5%. A study was conducted to assess the dosage of topical oxymetazoline solution required to elicit nipple erection and sensitivity. Five premenopausal subjects participated in the study. Subjects were not hypertensive, pregnant or breastfeeding. Three formulations were used: Formula A: 0.1% topical oxymetazoline hydrochloride solution; Formula B: 0.2% topical oxymetazoline hydrochloride solution; Formula C: 0.5% topical oxymetazoline hydrochloride solution.

The study was conducted over 3 days. On day 1, subjects were instructed to apply Formula A to both areolas. On day 2, subjects were instructed to apply Formula B to both areolas. On day 3, subjects were instructed to apply Formula C to both areolas. 0.1 mL of each formula was applied using a metered dosage dispenser to each areola. Table 8 summarizes the finding from this study. The 0.5% topical oxymetazoline solution (Formula C) elicited a clinical response in 4 out of 5 subjects while the 0.1% and 0.2% formulations (Formula A and B) failed to elicit a response. With the 0.5% topical oxymetazoline solution, response in nipple erection and sensitivity was obtained approximately within 1 hour and lasted over 8 hours.

TABLE 8

| Subject Nr. | Formula A | Formula B | Formula C |
|---|---|---|---|
| 1 | NR | NR | R |
| 2 | NR | NR | NR |
| 3 | NR | NR | R |

TABLE 8-continued

| Subject Nr. | Formula A | Formula B | Formula C |
|---|---|---|---|
| 4 | NR | NR | R |
| 5 | NR | NR | R |

R = response, i.e., nipple erection/increased sensitivity
NR = no response

Due to the long acting effect of oxymetaazoline it may be beneficial to apply once daily, every other day, or as needed prior to sexual activity or for restoration of sensation for patients that have lost or reduced sensitivity due to surgery or breast trauma.

Example 8

PhenylephrineHCl 15%. A study was conducted to evaluate the effect of PhenylephrineHCl 15% on the FSFI orgasm domain. Three premenopausal subjects participated in the study. Subjects were not hypertensive, pregnant or breastfeeding.

TABLE 9

Phenylephrine FSFI Orgasm Domain Study

| Subject Nr. | FSFI Scale How Often Orgasm was Reached Baseline | Intervention | FSFI Scale How Difficult to Reach Orgasm Baseline | Intervention |
|---|---|---|---|---|
| 1 | 2 | 4 | 4 | 5 |
| 2 | 1 | 4 | 3 | 4 |
| 3 | 2 | 5 | 2 | 5 |

In addition, 3 of 5 subjects that have previously reported to experience no increased sensitivity or nipple erection following application of 10% Phenylephrine HCl, have reported increased sensitivity and nipple erection following application of 15% Phenylephrine HCl. No adverse events were reported.

Due to the shorter lasting acting effect of phenylephrine compared to oxymetazoline it may be beneficial to apply as needed prior to sexual activity. However, due to report of nipple sensitivity as long as 12 hours past application, it may be beneficial to apply phenylephrine daily.

Example 9

Synephrine HCl 50%. A study was conducted to assess the dosage of topical synephrine solution required to elicit nipple erection and sensitivity. Five premenopausal subjects participated in the study. Subjects were not hypertensive, pregnant or breastfeeding. Two formulations were used: Formula A: 40% topical synephrine hydrochloride solution; Formula B: 50% topical synephrine hydrochloride solution.

The study was conducted over 2 days. On day 1, subjects were instructed to apply Formula A to both areolas. On day 2, subjects were instructed to apply Formula B to both areolas. 0.1 mL of each formula was applied using a metered dosage dispenser to each areola. Table 10 summarizes the finding from this study. The 50% topical synephrine hydrochloride solution (Formula B) elicited a clinical response in 4 out of 5 subjects while Formula A failed to elicit a response.

TABLE 10

Synephrine Study

| Subject Nr. | Formula A | Formula B |
|---|---|---|
| 1 | NR | R |
| 2 | NR | R |
| 3 | NR | R |
| 4 | NR | NR |
| 5 | NR | R |

NR = No Response
R = Response i.e., nipple erection/increased sensitivity

Example 10

Erection of the Nipple Areola Complex with 1% Phenylephrine Hydrochloride Solution In the following experiment, a commercially available iontophoresis patch was used to erect the nipple of a female subject.

1. The nipple and areola of each breast were prepared by cleaning with a sterile alcohol pad.
2. Two Inotopatch 80 (Travanti Medical) patches were removed from packaging.
3. The positive electrode of the first patch was filled with 1.3 mL of a 1% phenylephrine hydrochloride.
4. The negative electrode of the first patch was filled with 1.3 mL of a saline solution.
5. The positive electrode (approximately 1.5 cm diameter) containing the drug was placed over the nipple areola complex of the right breast; the negative electrode was placed on the adjacent breast tissue outside the nipple areola complex of the right breast.
6. Steps 2-5 were repeated, however, both electrodes of the Inotopatch 80 were filled with 1.3 mL of saline. The patch was applied to left breast following the procedure of step 5.
7. The patches were left in place (adhesive) for 1 hour (dosage=4.8 A, 80 mA/min).
8. After 1 hour the patches were removed.

After the experiment above, the patient's right nipple was visibly erect; the left nipple was not. The patient described increased sensitivity in the right nipple compared to the left nipple.

Example 11

Restoration of Nipple Sensitivity Post Breast Surgery. A case study was conducted to assess the efficacy of a topical phenylephrine solution in increasing nipple sensitivity in patients that reported a loss in nipple sensitivity post breast surgery. Five subjects ages 36-65 participated in the study. Subjects were asked to rate their nipple sensitivity on a Likert scale (1-10) before surgery and currently (i.e., after surgery). Next, patients were asked to apply a 10% phenylephrine solution to each nipple areola complex. 45 minutes after application of the drug, patients were asked again to rate their nipple sensitivity on a Likert scale (1-10). The results of the study are summarized in Table 11 below.

TABLE 11

|  |  |  |  | Nipple Sensitivity | | |
| --- | --- | --- | --- | --- | --- | --- |
| Patient | Age | Breast Size | Surgery Type | Pre-Surgery | Post-Surgery | Post-Surgery + Drug |
| 1 | 65 | 34 DD | Lumpectomy | 10 | 3 | 8 |
| 2 | 38 | 36 D | Augmentation | 9 | 5 | 8 |
| 3 | 42 | 36 C | Augmentation, Lift | 8 | 5 | 6 |
| 4 | 36 | 30 C | Augmentation | 8 | 6 | 6 |
| 5 | 52 | 38 C | Lumpectomy, Reduction, Partial Masectomy, Trans Flap | 7 | 0 | 1 |

Example 12

10%, 15% and 20% Phenylephrine Solutions Applied to Nipple-Areola Complex.

Method: 20 healthy, pre-menopausal females were recruited to the study. Subjects were instructed to apply either 4 or 6 drops of an investigational drug to each nipple areola complex. Baseline blood-pressure, heart rate, nipple erection, nipple sensitivity, genital lubrication and arousal were measured and recorded. 30 minutes later, blood pressure and heart rate were measured and recorded. 60 minutes later, blood-pressure, heart rate, nipple erection, nipple sensitivity, genital lubrication and arousal were measured and recorded.

During the study, four parameters of efficacy were measured: nipple erection, nipple sensitivity, genital lubrication, and arousal. Efficacy parameters were all patient reported outcomes measured at 0 and 60 minutes after the application of the investigational drug. Nipple erection was determined by asking the patient if they had experienced nipple erection during the 60 minutes after the application of the investigational drug. Nipple sensitivity was measured with a Likert scale of 1-10 (1 being "insensitive", 10 being "extremely sensitive/bordering on pain") at 0 and 60 minutes after the application of the investigational drug. Genital lubrication was measured with a Likert scale of 1-10 (1 being "none", 10 being "excellent") at 0 and 60 minutes after the application of the investigational drug. Arousal was measured with a Likert scale of 1-10 (1 being "none", 10 being "extremely aroused") at 0 and 60 minutes after the application of the investigational drug. A summary of the efficacy data is presented in the table below.

After a 48-hour washout period, subjects repeated the procedure using 4 or 6 drops of a new arm of the study. The subjects and the investigator were blinded to the drug assignment in each arm. In total 6 arms were tested:
Arm 1—Placebo, 4 drops
Arm 2—10% Phenylephrine HCl, 4 drops
Arm 3—15% Phenylephrine HCl, 4 drops
Arm 4—20% Phenylephrine HCl, 4 drops
Arm 5—Placebo, 6 drops
Arm 6—10% Phenylephrine HCl, 6 drops Results: The tables below shows the results of the study. There were no changes in blood pressure or heart rate of any of the subjects participating in the study. There was one adverse event (nipple pain) observed in the 20% Phenylephrine arm.

TABLE 12

| Nipple Erection and Sensitivity, Four Drops of Investigational Drug (0.114 mL) per NAC | | | | | | | | |
| --- | --- | --- | --- | --- | --- | --- | --- | --- |
|  | Placebo | | 10% PE | | 15% PE | | 20% PE | |
| Patient # | Erection | Sensitivity | Erection | Sensitivity | Erection | Sensitivity | Erection | Sensitivity |
| 1 | 0 | 2 | 0 | 0 | 0 | 0 | 1 | 4 |
| 2 | 0 | −1 | 0 | 0 |  |  | 0 | 2 |
| 3 | 0 | 1 | 1 | 1 | 0 | 2 | 1 | 2 |
| 4 | 0 | 0 | 0 | 0 | 1 | 3 | 0 | 0 |
| 5 | 0 | 0 | 0 | 1 | 1 | 0 | 1 | 0 |
| 6 | 0 | 1 | 0 | 1 | 1 | 2 | 1 | 1 |
| 7 | 0 | 0 | 1 | 0 | 0 | 0 | 0 | 0 |
| 9 | 0 | 1 | 1 | 5 | 1 | 5 | 1 | 1 |
| 10 | 0 | 0 | 0 | 0 | 0 | 2 | 1 | 2 |
| 11 | 0 | 0 | 0 | 1 | 0 | 0 | 0 | 0 |
| 12 | 0 | 0 | 0 | 0 | 0 | 0 |  |  |
| 13 | 0 | 0 | 1 | 2 | 0 | 2 | 1 | 2 |
| 14 | 0 | 0 | 0 | 0 | 0 | 0 | 0 | 0 |
| 15 | 0 | 0 | 0 | 0 | 0 | 1 | 1 | 1 |
| 16 | 0 | 0 | 1 | 1 | 1 | 3 | 1 | 4 |
| 17 | 0 | 0 | 1 | 2 | 1 | 9 | 1 | 9 |
| 19 | 0 | 0 | 1 | 0 | 0 | 0 | 1 | 2 |
| 20 | 0 | 0 | 0 | 1 | 1 | 1 | 1 | 1 |
| 21 |  |  |  |  | 1 | 2 | 0 | 0 |
| 22 | 0 | 0 | 1 | 1 | 1 | 3 | 1 | 0 |
| # Patients | 18 | 18 | 19 | 19 | 19 | 19 | 19 | 19 |
| Responders | 0 | 1 | 7 | 3 | 8 | 10 | 13 | 8 |
| % Responders | 0% | 6% | 37% | 16% | 42% | 53% | 68% | 42% |

TABLE 13

Nipple Erection and Sensitivity, Six Drops of Investigational Drug (0.170 mL) per NAC

| | Placebo | | 10% PE | |
|---|---|---|---|---|
| Patient # | Erection | Sensitivity | Erection | Sensitivity |
| 1 | 0 | 0 | 0 | 2 |
| 2 | | | | |
| 3 | 0 | 0 | 1 | 2 |
| 4 | 0 | 0 | 1 | 4 |
| 5 | 0 | 0 | 0 | 0 |
| 6 | 1 | 1 | 0 | 1 |
| 7 | 0 | 0 | 0 | 0 |
| 9 | 1 | 3 | 1 | 3 |
| 10 | 0 | 0 | 1 | 2 |
| 11 | | | 0 | 0 |
| 12 | 0 | 0 | 0 | 0 |
| 13 | 1 | 1 | 0 | 0 |
| 14 | 0 | 0 | 0 | 0 |
| 15 | 0 | 0 | | |
| 16 | 0 | 0 | 1 | 4 |
| 17 | | | 1 | 3 |
| 19 | 0 | 0 | 1 | 1 |
| 20 | | | 1 | 1 |
| 21 | | | | |
| 22 | | | | |
| # Patients | 14 | 14 | 16 | 16 |
| Responders | 3 | 1 | 8 | 7 |
| % Responders | 21% | 7% | 50% | 44% |

Tables 12 and 13 demonstrate the dose dependent increase in nipple sensitivity after application of the investigational drug. Nipple erection data was scored "1" for a positive response to the question "Did you experience nipple erection after applying the solution?" It was scored "0" otherwise. Sensitivity data was tabulated by subtracting the patient reported nipple sensitivity at 60 minutes from the reported value at baseline. Subjects were asked to rate their level of nipple sensitivity on a scale of 1-10 (1 being "non-sensitive" and 10 being "extremely sensitive, bordering on pain.") Subjects reporting a sensitivity increase greater than 2 after the application of each investigational drug were considered sensitivity responders.

TABLE 14

Change in heart rate 15, 30, and 60 minutes after the application of four drops of investigational drug (0.114 mL) per NAC

| | | Delta HR | | | | Delta HR | | |
|---|---|---|---|---|---|---|---|---|
| Patient # | HR (t = 0) | t = 15 | t = 30 | t = 60 | HR (t = 0) | t = 15 | t = 30 | t = 60 |
| | Placebo (Arm A) | | | | 10% (Arm C) | | | |
| 1 | 57 | −5 | 2 | −1 | 65 | −2 | 0 | −10 |
| 2 | 73 | −9 | −5 | −1 | 63 | −3 | −2 | −2 |
| 3 | 93 | −1 | −9 | −1 | 90 | −10 | −12 | −7 |
| 4 | 78 | −6 | 0 | −7 | 82 | 3 | 13 | −1 |
| 5 | 70 | 7 | −2 | −2 | 85 | −7 | −7 | −6 |
| 6 | 68 | 1 | −4 | 1 | 72 | 0 | −3 | −4 |
| 7 | 68 | 4 | −7 | −3 | 68 | 3 | −7 | −4 |
| 8 | 80 | 10 | 7 | 8 | 74 | 0 | −1 | −1 |
| 9 | 63 | −4 | −9 | 0 | 60 | 3 | 5 | 5 |
| 10 | 80 | −7 | 1 | −3 | 68 | −1 | 7 | 5 |
| 11 | 73 | −5 | −6 | −8 | 71 | −2 | −3 | −8 |
| 12 | 96 | 2 | −4 | −7 | 74 | 3 | 3 | 7 |
| 13 | 85 | −2 | −5 | 2 | 85 | 4 | 3 | 2 |
| 14 | 102 | −3 | −9 | −13 | 96 | −9 | −4 | 2 |
| 15 | 65 | −6 | −4 | −6 | 66 | −3 | −4 | −1 |
| 16 | 80 | −10 | −10 | −12 | 77 | −2 | −4 | −9 |
| 17 | 61 | −6 | −5 | −5 | 61 | −1 | −1 | −4 |
| 18 | 88 | 0 | −1 | 0 | 83 | 6 | −7 | −2 |
| 19 | 68 | −1 | −3 | 6 | 74 | −5 | 0 | −4 |
| 20 | 87 | −3 | −8 | −2 | 85 | 0 | 7 | −6 |
| | 15% (Arm D) | | | | 20% (Arm B) | | | |
| 1 | 77 | −9 | −14 | −16 | 84 | −15 | −20 | −21 |
| 2 | 63 | 1 | 4 | 4 | 64 | 3 | 4 | 3 |
| 3 | 96 | 0 | 0 | −6 | 84 | −2 | −6 | 1 |
| 4 | 77 | −4 | −1 | −2 | 79 | −1 | −14 | −13 |
| 5 | 82 | −6 | −2 | −4 | 71 | −2 | −3 | −21 |
| 6 | 71 | 4 | 6 | −2 | 82 | −6 | 7 | 6 |
| 7 | 80 | −15 | −10 | −7 | 70 | 2 | 1 | −1 |
| 8 | 89 | −9 | −10 | −9 | 81 | −4 | 7 | 0 |
| 9 | 80 | −4 | −4 | 1 | 80 | −10 | −1 | −8 |
| 10 | 82 | −8 | −5 | −3 | 82 | 6 | −7 | −6 |
| 11 | 82 | −5 | −2 | −2 | 66 | 1 | 10 | 4 |
| 12 | 79 | −3 | 2 | 0 | 80 | −7 | −9 | 0 |
| 13 | 92 | −9 | −12 | −10 | 82 | −5 | 1 | −3 |
| 14 | 87 | 6 | 8 | −6 | 102 | −6 | −1 | −4 |
| 15 | 71 | −1 | 5 | −3 | 61 | −1 | 3 | 4 |
| 16 | 72 | −2 | −2 | −2 | 60 | 10 | 10 | 11 |
| 17 | 55 | 1 | 1 | 2 | 61 | −4 | −3 | −3 |

TABLE 14-continued

Change in heart rate 15, 30, and 60 minutes after the application of four drops of investigational drug (0.114 mL) per NAC

| Patient # | HR (t = 0) | Delta HR t = 15 | t = 30 | t = 60 | HR (t = 0) | Delta HR t = 15 | t = 30 | t = 60 |
|---|---|---|---|---|---|---|---|---|
| 18 | 76 | −3 | 4 | 0 | 99 | −3 | −9 | −6 |
| 19 | 76 | −3 | 3 | −6 | 67 | 7 | 6 | 9 |
| 20 | 80 | −9 | −8 | −11 | 71 | 0 | 1 | −2 |

TABLE 15

Genital lubrication and arousal, 60 minutes after the application of different phenylephrine solutions.

| Patient # | Placebo (Arm A) Lubrication | Arousal | 10% (Arm C) Lubrication | Arousal | 15% (Arm D) Lubrication | Arousal | 20% (Arm B) Lubrication | Arousal |
|---|---|---|---|---|---|---|---|---|
| 1 | 0 | 0 | 0 | 0 | 0 | 0 | 1 | 1 |
| 2 | −1 | −1 | 0 | 0 | 1 | 0 | 0 | 0 |
| 3 | 1 | 0 | 1 | 0 | 3 | 0 | 3 | 0 |
| 4 | 0 | 0 | 0 | 0 | 0 | 0 | 0 | 0 |
| 5 | 0 | 0 | 0 | 0 | 0 | 0 | 0 | 0 |
| 6 | 0 | 0 | 0 | 0 | 0 | 0 | 0 | 0 |
| 7 | −2 | 0 | 0 | 0 | 0 | 0 | 2 | 0 |
| 8 | 1 | 0 | 1 | 0 | 2 | 0 | 0 | 0 |
| 9 | 0 | 0 | 0 | 0 | 0 | 0 | 0 | 0 |
| 10 | 0 | 0 | 0 | 0 | 0 | 0 | 0 | 0 |
| 11 | 0 | 0 | 0 | 0 | 0 | 0 | 0 | 0 |
| 12 | 0 | 0 | 0 | 0 | 0 | 0 | 0 | 0 |
| 13 | 0 | 0 | 0 | 0 | 0 | 0 | 0 | 0 |
| 14 | 1 | 0 | 0 | 0 | 1 | 0 | 2 | 0 |
| 15 | 0 | 0 | 0 | 0 | 0 | 0 | 0 | 0 |
| 16 | 0 | 0 | 0 | 0 | 0 | 0 | 2 | 0 |
| 17 | 0 | 0 | 0 | 0 | 0 | −1 | 0 | 0 |
| 18 | 0 | 0 | 0 | 0 | 0 | 0 | 0 | 0 |
| 19 | 0 | 0 | 2 | 0 | 0 | 0 | 0 | 0 |
| 20 | 0 | 0 | 0 | 0 | 1 | 0 | 0 | 0 |
| # Patients | 20 | 20 | 20 | 20 | 20 | 20 | 20 | 20 |
| Responders | 0 | 0 | 1 | 0 | 2 | 0 | 4 | 0 |
| Percent | 0% | 0% | 5% | 0% | 10% | 0% | 20% | 0% |

Genital lubrication was measured with a Likert scale of 1-10 (1 being "none" and 10 being "excellent") at 0 and 60 minutes after the application of the investigational drug. Arousal was measured with a Likert scale of 1-10 (1 being "none" and 10 being "extremely aroused") at 0 and 60 minutes after the application of the investigational drug. Data are displayed as change from baseline of the reported values. A subject was considered a responder for genital lubrication if she reported a change in genital lubrication of 2 or more. A subject was considered a responder for arousal if she reported a change in arousal of 2 or more.

The invention claimed is:

1. A method of treating female sexual dysfunction, the method comprising applying a therapeutically effective amount of a composition comprising an alpha-1 adrenergic receptor agonist topically to a nipple-areola complex of a female subject in need of such treatment, wherein the composition is applied in a sufficient amount to increase nipple sensitivity.

2. The method of claim 1, wherein the alpha-1 adrenergic receptor agonist is phenylephrine.

3. The method of claim 1, wherein the composition is applied in a sufficient amount to cause erection of the nipple.

4. The method of claim 1, wherein 0.2-0.8 mg/cm2 of the alpha-1 adrenergic receptor agonist is applied.

5. The method of claim 4, wherein the alpha-1 adrenergic receptor agonist is phenylephrine.

6. The method of claim 1, wherein the female sexual dysfunction is selected from the group consisting of female sexual arousal disorder (FSAD), female sexual interest/arousal disorder (FSIAD), female orgasmic disorder (FOD) and female hypoactive sexual desire disorder (FHSDD).

7. A method of reducing or alleviating a symptom of female sexual dysfunction, the method comprising applying a therapeutically effective amount of a composition comprising an alpha-1 adrenergic receptor agonist topically to a nipple-areola complex of a female subject in need of such treatment, wherein the composition is applied in a sufficient amount to increase nipple sensitivity.

8. The method of claim 7, wherein the symptom of female sexual dysfunction is a symptom of female hypoactive sexual desire disorder (FHSDD), female sexual interest/arousal disorder (FSIAD), female orgasmic disorder (FOD) or female sexual arousal disorder (FSAD).

9. The method of claim 7, wherein the symptom of female sexual dysfunction is a symptom of female sexual interest/arousal disorder selected from the group consisting of (1) absent/reduced interest in sexual activity; (2) absent/reduced sexual/erotic thoughts or fantasies; (3) no/reduced initiation of sexual activity, and typically unreceptive to a partner's attempts to initiate; (4) absent/reduced sexual excitement/pleasure during sexual activity in almost all or all sexual encounters; (5) absent/reduced sexual interest/arousal in response to any internal or external sexual/erotic cues; and (6) absent/reduced genital or nongenital sensations during sexual activity in almost all or all sexual encounters.

10. The method of claim 7, wherein the alpha-1 adrenergic receptor agonist is phenylephrine.

11. The method of claim 7, wherein the composition is applied in a sufficient amount to cause erection of the nipple.

12. The method of claim 7, wherein 0.2-0.8 mg/cm2 of the alpha-1 adrenergic receptor agonist is applied.

13. The method of claim 12, wherein the alpha-1 adrenergic receptor agonist is phenylephrine.

14. A method for enhancing sexual satisfaction in a female subject, comprising applying an effective amount of a composition comprising an alpha-1 adrenergic receptor agonist topically to a nipple-areola complex of the female subject, wherein the composition is applied in a sufficient amount to increase nipple sensitivity.

15. The method of claim 14, wherein the alpha-1 adrenergic receptor agonist is phenylephrine.

16. The method of claim 14, wherein the composition is applied in a sufficient amount to cause erection of the nipple.

17. The method of claim 14, wherein 0.2-0.8 mg/cm2 of the alpha-1 adrenergic receptor agonist is applied.

18. The method of claim 17, wherein the alpha-1 adrenergic receptor agonist is phenylephrine.

19. The method of claim 14, wherein the composition is in or on an iontophoresis patch and the patch is placed on the nipple of the female subject.

20. A method of causing erection of nipples, increasing nipple sensitivity, increasing duration of orgasm, reducing time to orgasm, and/or increasing oxytocin release related to sexual activity in a female subject comprising applying an effective amount of a composition comprising an alpha-1 adrenergic receptor agonist topically to a nipple-areola complex of the female subject, wherein the composition is applied in a sufficient amount to increase nipple sensitivity.

21. The method of claim 20, wherein the alpha-1 adrenergic receptor agonist is phenylephrine.

22. The method of claim 20, wherein the composition is applied in a sufficient amount to cause erection of the nipple.

23. The method of claim 20, wherein 0.2-0.8 mg/cm2 of the alpha-1 adrenergic receptor agonist is applied.

24. The method of claim 23, wherein the alpha-1 adrenergic receptor agonist is phenylephrine.

25. The method of claim 1, wherein the alpha 1 adrenergic receptor agonist is applied within one hour prior to a sexual activity.

26. The method of claim 1, wherein the subject is a premenopausal female.

27. The method of claim 1, wherein the alpha-1 adrenergic receptor agonist is oxymetazoline.

28. The method of claim 1, wherein the alpha-1 adrenergic receptor agonist is oxymetazoline and is administered in a composition comprising 0.05-5.0% by weight of oxymetazoline.

29. The method of claim 1, wherein the alpha-1 adrenergic receptor agonist is synephrine.

30. A method of treating female sexual dysfunction, the method comprising applying a therapeutically effective amount of a composition comprising norepinephrine topically to a nipple-areola complex of a female subject in need of such treatment, wherein the composition is applied in a sufficient amount to increase nipple sensitivity.

31. A method of treating female nipple neuropathy, the method comprising applying a therapeutically effective amount of a composition comprising an alpha-1 adrenergic receptor agonist topically to a nipple-areola complex of a female subject in need of such treatment, wherein the composition is applied in a sufficient amount to increase nipple sensitivity.

32. The method of claim 31, wherein the alpha-1 adrenergic receptor agonist is phenylephrine.

33. The method of claim 31, wherein the composition is applied in a sufficient amount to cause erection of the nipple.

34. The method of claim 31, wherein 0.2-0.8 mg/cm2 of the alpha-1 adrenergic receptor agonist is applied.

35. The method of claim 31, wherein the alpha-1 adrenergic receptor agonist is phenylephrine.

36. The method of claim 31, wherein the alpha 1 adrenergic receptor agonist is applied within one hour prior to a sexual activity.

37. The method of claim 31, wherein the subject is a premenopausal female.

38. The method of claim 31, wherein the alpha-1 adrenergic receptor agonist is oxymetazoline.

39. The method of claim 31, wherein the alpha-1 adrenergic receptor agonist is oxymetazoline and is administered in a composition comprising 0.05-5.0% by weight of oxymetazoline.

40. The method of claim 31, wherein the alpha-1 adrenergic receptor agonist is synephrine.

41. A method of treating female lost or reduced nipple sensitivity due to breast trauma due to injury or as a result of surgery, the method comprising applying a therapeutically effective amount of a composition comprising an alpha-1 adrenergic receptor agonist topically to a nipple-areola complex of a female subject in need of such treatment, wherein the composition is applied in a sufficient amount to increase nipple sensitivity.

42. The method of claim 41, wherein the alpha-1 adrenergic receptor agonist is phenylephrine.

43. The method of claim 41, wherein the composition is applied in a sufficient amount to cause erection of the nipple.

44. The method of claim 41, wherein 0.2-0.8 mg/cm2 of the alpha-1 adrenergic receptor agonist is applied.

45. The method of claim 41, wherein the alpha-1 adrenergic receptor agonist is phenylephrine.

46. The method of claim 41, wherein the alpha 1 adrenergic receptor agonist is applied within one hour prior to a sexual activity.

47. The method of claim 41, wherein the subject is a premenopausal female.

48. The method of claim 41, wherein the alpha-1 adrenergic receptor agonist is oxymetazoline.

49. The method of claim 41, wherein the alpha-1 adrenergic receptor agonist is oxymetazoline and is administered in a composition comprising 0.05-5.0% by weight of oxymetazoline.

50. The method of claim 41, wherein the alpha-1 adrenergic receptor agonist is synephrine.

* * * * *